US012558326B2

(12) United States Patent
Sherrington et al.

(10) Patent No.: US 12,558,326 B2
(45) Date of Patent: Feb. 24, 2026

(54) METHOD FOR TREATING EPILEPSY

(71) Applicant: Xenon Pharmaceuticals Inc., Burnaby (CA)

(72) Inventors: Robin Paul Sherrington, North Vancouver (CA); Jean-Jacques Alexandre Cadieux, Burnaby (CA); Parisa Karimi Tari, Vancouver (CA); Jeffrey Paul Bechard, Surrey (CA)

(73) Assignee: Xenon Pharmaceuticals Inc., Burnaby (CA)

( * ) Notice: Subject to any disclaimer, the term of this patent is extended or adjusted under 35 U.S.C. 154(b) by 995 days.

(21) Appl. No.: 16/523,568

(22) Filed: Jul. 26, 2019

(65) Prior Publication Data

US 2020/0030260 A1 Jan. 30, 2020

Related U.S. Application Data

(60) Provisional application No. 62/711,051, filed on Jul. 27, 2018.

(51) Int. Cl.
*A61K 31/137* (2006.01)
*A61K 31/24* (2006.01)
*A61P 25/08* (2006.01)

(52) U.S. Cl.
CPC ............ *A61K 31/137* (2013.01); *A61K 31/24* (2013.01); *A61P 25/08* (2018.01)

(58) Field of Classification Search
CPC ........ A61K 31/137; A61K 31/24; A61P 25/08
See application file for complete search history.

(56) References Cited

U.S. PATENT DOCUMENTS

| | | | |
|---|---|---|---|
| 3,198,833 A | 8/1965 | Beregi et al. | |
| 3,607,909 A | 9/1971 | Beregi et al. | |
| 3,845,770 A | 11/1974 | Theeuwes et al. | |
| 4,326,525 A | 4/1982 | Swanson et al. | |
| 5,587,398 A | 12/1996 | Elmaleh et al. | |
| 6,416,780 B1 | 7/2002 | Passmore et al. | |
| 9,925,172 B2 * | 3/2018 | Baraban | A61K 45/06 |
| 2017/0071949 A1 | 3/2017 | De Witte et al. | |
| 2018/0325909 A1 | 11/2018 | De Witte et al. | |

FOREIGN PATENT DOCUMENTS

| | | |
|---|---|---|
| FR | 1658 M | 1/1963 |
| JP | 2016-216438 A | 12/2016 |
| JP | 2017-51788 A | 3/2017 |
| JP | 2017-57188 A | 3/2017 |
| WO | 98/50016 A2 | 11/1998 |
| WO | 2016/138138 A1 | 9/2016 |

OTHER PUBLICATIONS

"Neurological Diagnostic Tests and Procedures" at the website of the National Institute of Neurological Disorders and Stroke, National Institutes of Health, Bethesda, MD, www.ninds.nih.gov/disorders/misc/diagnostic_tests.htm (2019).
Barton et al., 2001 Epilepsy Res. 47(3):217-227.
Berg et al., "Revised terminology and concepts for organization of seizures and epilepsies: Report of the ILAE Commission on Classification and Terminology 2005-2009," 2010 Epilepsia 51(4):676-685.
Berkow et al., eds., The Merck Manual, 19th edition, Merck and Co., Rahway, N.J. (2011).
Bouilleret et al., 1999 Neuroscience 89(3):717-729.
Brown et al., 1953 J. Pharmacol. Exp. Therapeut. 107(3):273-283.
Brunton et al., eds., Goodman and Gilman's the Pharmacological Basis of Therapeutics, 12th edition, McGraw-Hill 2011.
Claes et al., "De Novo Mutations in the Sodium-Channel Gene SCN1A Cause Severe Myoclonic Epilepsy of Infancy," 2001 Am. J. Hum. Genet. 68:1327-1332.
Coleman et al., 1985 Life Sci. 37(8):749-755.
Desarro et al., 2017 Epilepsy Behav. 71:165-173.
Dinday et al., 2015 ENEURO 2(4) e0068-15.2015 1-19.
Dürmüller et al., Neuroreport 4(6):683-686.
Han et al., 2012 Nature 489:385.
Hartman et al., 2008 Epilepsia 49(2):334-339.
International Search Report and Written Opinion corresponding to International Application No. PCT/US2019/043765 dated Jan. 30, 2020.
Kuzma et al., Regional Anesthesia 1997, 22(6):543-551.
Lawrence et al., 2000 Molecular Pharmacology, 57:75-81.
Li, J., et al., "Antiepileptic effect of the enantiomers of fenfluramineand norfenfluraminein a Dravet zebrafish model," Zogenix Ku Leuven, Presented at the American Epilepsy Society (AES) Annual Meeting, Nov. 30-Dec. 4, 2018, New Orleans, LA (Poster).
Lothman and Williamson 1994 Brain Res. 649(1-2):71-84.
Lothman, E.W. 1988 Epilepsy Res. 2(6):367-379.
Macdonald RL, Meldrum BS. Principles of antiepileptic drug action. In Antiepileptic Drugs, Fourth Edition. Levy RH, Mattson RG, Meldrum BS, eds. New York: Raven Press, 1995:61-77.
Marini et al., 2011 Epilepsia 52 (Suppl.2):24-29.
Mistry et al., 2014 Neurobiol. Dis. 65:1-11.
Nabbout, R., et al., "Fintepla® (Fenfluramine HCI Oral Solution) Reduces Convulsive Seizure Frequency in Dravet Syndrome Patients Receiving an Antiepileptic Drug Treatment Regimen Containing Stiripentol: A Phase 3, Randomized, Placebo-Controlled Clinical Study," Presented at the American Epilepsy Society (AES) Annual Meeting, Nov. 30-Dec. 4, 2018, New Orleans, LA (poster).

(Continued)

*Primary Examiner* — Sahar Javanmard
(74) *Attorney, Agent, or Firm* — Wolf, Greenfield & Sacks, P.C.

(57) ABSTRACT

In certain embodiments, the present disclosure is directed to methods and uses for treating a mammal having an epileptic seizure disorder or being at risk for having an epileptic seizure disorder, comprising administering certain herein disclosed isolated fenfluramine enantiomers that are surprisingly effective as anti-epilepsy drugs (AEDs), despite having lower anti-seizure potency than fenfluramine racemate, by virtue of also being less cardiotoxic than fenfluramine racemate. Preferred embodiments contemplate treatment of Dravet syndrome; other preferred embodiments contemplate treatment of other epileptic seizure disorders.

23 Claims, 2 Drawing Sheets

(56) References Cited

OTHER PUBLICATIONS

Figure 1:
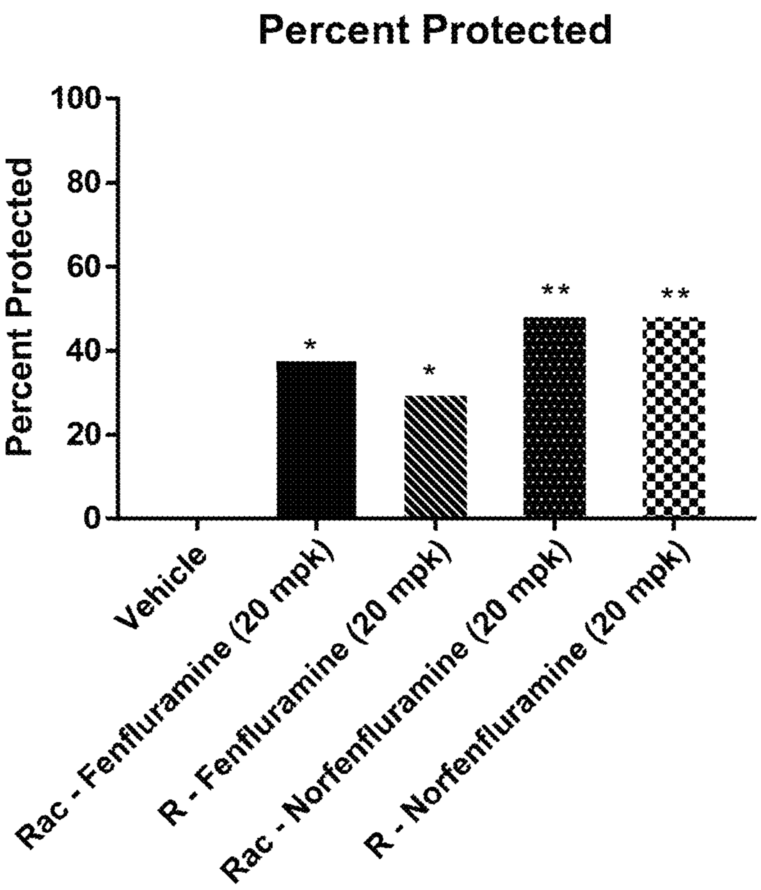

Newland and Cull-Candy 1992 J. Physiol. 447(1):191-213.
Oakley et al., (2009) Proc. Natl. Acad. Sci. U.S.A. 106(10):3994-3999.
Oakley et al., (2013) J. Pharmacol. Exp. Ther. 345(2):215-224.
Porter et al., "Functional characterization of agonists at recombinant human 5-HT2A, 5-HT2B and 5-HT2C receptors in CHO-KI cells," 1999 Brit. J of Pharmacology 128:13-20.
Racine, R.J. 1972 Electroencephalogr. Clin. Neurophysiol. 32(3):281-294.
Riban et al., 2002 Neuroscience 112(1):101-111.
Rowley et al., 2010 Epilepsy Res. 92(2-3):163-169.
Shih et al., 2001 Toxicol. 162(1):35-42.
Snodgrass, S.R. 1992 J. Child Neurol. 7(1):77-86.
Striano et al., 2016 Pharmacol. Res. 107:426-429.
Suzuki et al., 1995 Neuroscience 64(3):665-674.
Swinyard et al., 1993 Epilepsy Res. 15(1):35-45.
Swinyard, E.A., 1969 Epilepsia 10(2):107-119.
Swinyard, E.A., Experimental Models of Epilepsy: A Manual for the Laboratory Worker, in Electrically Induced Convulsions, eds. J.K.P. D.P Purpura, D. Tower, D.M. Woodbry, R. Walter. 1972, New York: Raven Press, pp. 433-438.
Swinyward, E.A. Electrically induced convulsions, in Experimental Models of Epilepsy, D.B. Purpura, et al., Editors. 1972, Raven Press: New York. pp. 443-458.
The Science and Practice of Pharmacy, 20th Edition (Philadelphia College of Pharmacy and Science, 2000.
Toman et al., 1952 Texas Reports on Biology and Medicine 10:96.
White et al., 1997 Epilepsy Res. 28:167.
White et al., 2012 Epilepsia 53(1):134-146.
White HS, Woodhead JH, Wilcox KS, General principles: discovery and preclinical development of antiepileptic drugs, In: Levy RH, Mattson RH, Meldrum BS, Perucca E, editors. Antiepileptic drugs 5th ed Philadelphia: Lippincott Williams & Wilkins; 2002. pp. 36-48.
Wood, J.D. 1975 Prog. Neurobiol. 5:77-95.
Wright et al., 2016 Molec. Genet. Genom. Med. 4(2):197.
Yu et al., 2006 Nat. Neurosci. 9:1142-1149.
Andrejak et al., "Drug-induced valvular heart disease: An update," *Archives of Cardiovascular Disease* 106:333-339, 2013.
Boel et al., "Add-On Therapy of Fenfluramine in Intractable Self-Induced Epilepsy," *Neuropediatrics* 27:171-173, 1996.
Cambon et al., "Clinical and echographic characteristics of patients exposed to fenfluramin or its derivatives: Results of a prospective, single-centre, observational study," *Archives of Cardiovascular Disease* 108:172-180, 2015.
Ceulemans et al., "Successful use of fenfluramine as an add-on treatment for Dravet syndrome," *Epilepsia* 53(7):1131-1139, 2012.
Coquerel et al., "Optical Resolution of (±)-Fenfluramine and (±)-Norfenfluramine by Preferential Crystallization," *Chemistry Letters*, pp. 1081-1084, 1988.
Elangbam et al., "5-Hydroxytryptamine (5HT)-induced valvulopathy: Compositional valvular Alterations are associated with 5HT2B receptor and 5HT transporter transcript changes in Sprague-Dawley rats," *Experimental and Toxicologic Pathology* 60:253-262, 2008.
Fitzgerald et al., "Possible Role of Valvular Serotonin 5-$HT_{2B}$ Receptors in the Cardiopathy Associated with Fenfluramine," *Molecular Pharmacology* 57:75-81, 2000.
Gentsch et al., "Fenfluramine Blocks Low-$Mg^{2+}$-Induced Epileptiform Activity in Rat Entorhinal Cortex," *Epilepsia* 41(8):925-928, 2000.
Lagae et al., "ZX008 (Fenfluramine HCI Oral Solution) in Dravet Syndrome: Results of a Phase 3, Randomized, Double-Blind, Placebo-Controlled Trial," $71^{st}$ Annual Meeting of the American Epilepsy Society, Washington, D.C., Dec. 1-5, 2017, 1 page. (Poster).
Porter et al., "Functional characterization of agonists at recombinant human 5-$HT_{2A}$, 5-$HT_{2B}$ and 5-$HT_{2C}$ receptors in CHO-K1 cells," *British Journal of Pharmacology* 128:13-20, 1999.
Rothman et al., "Serotonin releasing agents Neurochemical, therapeutic and adverse effects," *Pharmacology, Biochemistry and Behavior* 71:825-836, 2002.
Rothman et al., "(+)-Fenfluramine and Its Major Metabolite, (+)-Norfenfluramine, Are Potent Substrates for Norepinephrine Transporters," *The Journal of Pharmacology and Experimental Therapeutics* 305(3):1191-1999, 2003.
Bermack et al., "Modulation of serotonergic neurotransmission by short- and long-term treatments with sigma ligands," British Journal of Pharmacology (2001) 134, 691-699.
Guo et al., "Allosteric modulation of sigma-1 receptors elicits anti-seizure activities," British Journal of Pharmacology (2015), 172, 4052-4065.
International Preliminary Report on Patentability corresponding to International Application No. PCT/US2019/043765 dated Feb. 2, 2021.
Sourbron et al., "Pharmacological Analysis of the Anti-epileptic Mechanisms of Fenfluramine in scn1a Mutant Zebrafish," Frontiers in Pharmacology (2017) vol. 8, Article 191, pp. 1-13.
Gharedaghi et al., The role of different serotonin receptor subtypes in seizure susceptibility. Exp. Brain Res. (2014) 232:347-367. doi: 10.1007/s00221-013-3757-0.
Hyttel et al., The pharmacological effect of citalopram residues in the (S)-(+)-enantiomer. J. Neural Transm. [Gen Sec] (1992) 88:157-160. doi: 10.1007/BF01244820.
Li et al., Dose-effect of fenfluramine use on the severity of valvular heart disease among fen-phen patients with valvulopathy. Int. J. Obesity (1999) 23:926-928. doi: 10.1038/sj.ijo.0801020.
Odi et al., Fenfluramine repurposing from weight loss to epilepsy: What we do and do not know. Pharmacol. & Therapeutics (2021) 226 107866. doi: 10.1016/j.pharmthera.2021.107866.
Martin et al., An Examination of the Mechanism of Action of Fenfluramine in Dravet Syndrome: A Look beyond Serotonin. Biological Psychiatry. Abstract 663. (May 15, 2017) 81:S268.

* cited by examiner

METHOD FOR TREATING EPILEPSY

1. FIELD

The present disclosure is directed to the use of the (R)-enantiomer of fenfluramine or its active metabolite, norfenfluramine, or a prodrug thereof for treating epilepsy, including Dravet syndrome.

2. BACKGROUND

Epilepsy and epileptic seizure disorders represent a class of neurological diseases, disorders and conditions that are estimated to afflict over 65 million people globally, including at least three million in the United States. Approximately 150,000 new cases of epilepsy are reported in the United States each year. Epileptic seizure disorders are chronic conditions characterized by sporadic generalized or focal seizures of widely varying frequency, intensity and duration (e.g., Berg et al., 2010 *Epilepsia* 51(4):676-685). Epileptic seizures may be manifest as one or more of transient convulsions, cessation of breathing, loss of consciousness, impaired speech or motor abilities, loss of postural tone, involuntary muscle contractions, or other consequences of abnormal and excessive signal transmission by cortical neurons of the central nervous system (CNS). Epileptic seizures can thus impair an individual's ability to safely perform routine activities such as walking, swimming or driving, or may be the underlying cause of bodily injuries such as bruises, cuts, burns, orthopedic injuries, injuries from falls, etc. More dramatically, epileptic seizures may occasionally result in Sudden Unexpected Death in Epilepsy (SUDEP), of which there are an estimated 40,000 cases in the United States each year.

A large number of epileptic seizure disorders have been characterized and classified, including partial seizures (such as simple, complex, secondary generalized, and focal onset), generalized seizures (such as absence, myoclonic, atonic, tonic and tonic clonic), and disorders including photosensitive epilepsy, self-induced syncope, intractable epilepsy, Angelman syndrome, benign rolandic epilepsy, CDKL5 disorder, childhood and juvenile absence epilepsy, Dravet syndrome, frontal lobe epilepsy, Glut1 deficiency syndrome, hypothalamic hamartoma, infantile spasms/West's syndrome, juvenile myoclonic epilepsy, Landau-Kleffner syndrome, Lennox-Gastaut syndrome (LGS), epilepsy with myoclonic-absences, Ohtahara syndrome, Panayiotopoulos syndrome, PCDH19 epilepsy, progressive myoclonic epilepsies, Rasmussen's syndrome, ring chromosome 20 syndrome, reflex epilepsies, temporal lobe epilepsy, Lafora progressive myoclonus epilepsy, neurocutaneous syndromes, tuberous sclerosis complex, early infantile epileptic encephalopathy, early onset epileptic encephalopathy, generalized epilepsy with febrile seizures plus (GEFS+), Rett syndrome, multiple sclerosis, Alzheimer's disease, autism, ataxia, hypotonia and paroxysmal dyskinesia.

Approximately 25 anti-epilepsy drugs (AEDs) have been developed to control or treat epileptic seizures, many of which AEDs act in the CNS as non-selective sodium channel blockers. (Macdonald R L, Meldrum B S. Principles of antiepileptic drug action. In *Antiepileptic Drugs*, Fourth Edition. Levy R H, Mattson R G, Meldrum B S, eds. New York: Raven Press, 1995:61-77). Responsiveness to AEDs, however, varies among patients, making it difficult to predict the efficacy of any particular AED in a given subject: None of the AEDs are regarded as a cure for any epileptic seizure disorder. Moreover, AEDs are ineffective in approximately one-third of epilepsy patients, prompting recognition that multiple distinct genetic defects underlie the different epileptic seizure disorders (e.g., Striano et al., 2016 *Pharmacol. Res.* 107:426-429).

Dravet syndrome, also known as severe myoclonic epilepsy in infancy (SMEI), is an epileptic seizure disorder that was first described in 1978 (Dravet, 1978 *Vie Méd* 8:543-548). Dravet syndrome occurs with an approximate birth rate of between one in 40,000 and one in 20,000 and is characterized by a seizure in the first year of life, often initially provoked by a fever, with subsequent seizures not necessarily being triggered by fever. Patients with Dravet syndrome may suffer from frequent and unpredictable seizures, temperature- or photosensitivity-induced seizures, motor abnormalities, and/or impaired, arrested or regressive mental development.

A genetic defect in a neuron-specific voltage-gated sodium channel (SCN1A) was identified in 2001 as an underlying cause of most (but not all) cases of Dravet syndrome (Claes et al., 2001 *Am. J. Hum. Genet.* 68:1327-1332; Marini et al., 2011 *Epilepsia* 52(Suppl. 2):24-29; Ceulemans et al., 2012 *Epilepsia* 53(7): 1131-1139). Accordingly, AEDs having neuronal sodium channel-blocking activity including SCN1A as their mechanism of action are contraindicated for the treatment of Dravet syndrome.

Fenfluramine ((R/S)—N-ethyl-1-[3-(trifluoromethyl)phenyl]propan-2-amine) is an appetite-suppressing amphetamine-like drug that exists as a racemic mixture of two enantiomers, and was marketed for over 20 years in a formulation with phentermine (2-methyl-1-phenylpropan-2-amine) as an anti-obesity medicine. Fenfluramine is able to cross the blood-brain barrier (BBB) and increases serotonin (5-hydroxytryptamine, 5-HT) levels in the CNS by disrupting vesicular 5-HT stores and by reversing 5-HT uptake via selective serotonin transporters. These serotonergic effects are believed to underlie the appetite-suppressing properties of fenfluramine, and have also been investigated for potential anti-epileptic effects in an in vitro rat induced rat entorhinal cortex model (Gentsch et al., 2000 *Epilepsia* 41(8):925-928).

Fenfluramine was withdrawn from the pharmaceuticals market, however, when it was found to be responsible for adverse cardiovascular effects, including cardiac valve hypertrophy, pulmonary hypertension and cardiac fibrosis resulting from fenfluramine agonist activity via the serotonin receptor 5-HT2B that is expressed in cardiac tissue (Andrejak et al., *Arch. Cardiovascular Dis.* (2013) 106:333-339; Elangbam et al., *Exp Toxicol Pathol* (2008) 60(4-5):253-262; Cambon et al., *Arch Cardiovascular Dis* (2015) 108: 172-180). Fenfluramine has exhibited a degree of apparent efficacy—via its major metabolite norfenfluramine—in limiting the frequency or severity of seizures in cohorts of Dravet syndrome patients (Ceulemans et al., 2012; Boel et al., 1996 *Neuropediatrics* 27:171-173; Lagae, L. et al., "ZX008 (Fenfluramine HCl Oral Solution) in Dravet Syndrome: Results of a Phase 3, Randomized, Double-Blind, Placebo-Controlled Trial," Poster No. 2.434, American Epilepsy Society Annual Meeting, Dec. 1-5, 2017), but remains unavailable as an AED due to its history of cardiotoxicity. The structurally related compound benfluorex ((R/S)-2-(1-(3-(trifluoromethyl)phenyl)propan-2-ylamino)ethyl benzoate), which is also a racemic mixture of two enantiomers, is a prodrug of norfenfluramine that similarly promotes 5-HT release (having agonist activity on 5HT2 receptors via its metabolite norfenfluramine) and was marketed as an anti-diabetic agent for a time before it, too, was withdrawn due to adverse cardiovascular effects analogous to those associated with fenfluramine. Benfluorex, however, has not previously been investigated as an AED.

Clearly there remains a need in the art for effective treatments for epilepsy and other epileptic seizure disorders, including Dravet syndrome. The present disclosure addresses this need by providing compositions and methods for treating epileptic seizure disorders, and offers other related advantages.

3. SUMMARY

The present disclosure is directed in certain embodiments to the use of the (R)-enantiomer of fenfluramine, the (R)-enantiomer of benfluorex, or the (R)-enantiomer of fenfluramine's or of benfluorex's active metabolite, norfenfluramine or a prodrug thereof, for treating or preventing epilepsy, including Dravet syndrome.

Accordingly, in one embodiment, the disclosure provides a method of treating or preventing an epileptic seizure disorder in a mammal, comprising administering to the mammal a therapeutically effective amount of one, two or all three of: (i) (R)-fenfluramine or a pharmaceutically acceptable salt, solvate or prodrug thereof, (ii) (R)-norfenfluramine or a pharmaceutically acceptable salt, solvate or prodrug thereof, and (iii) (R)-benfluorex or a pharmaceutically acceptable salt, solvate or prodrug thereof, wherein (R)-fenfluramine is substantially free of (S)-fenfluramine (e.g., greater than 80% ee), (R)-norfenfluramine is substantially free of (S)-norfenfluramine (e.g., greater than 80% ee), and (R)-benfluorex is substantially free of (S)-benfluorex (e.g., greater than 80% ee). In certain embodiments there is provided a method of treating a mammal having or at risk for having an epileptic seizure disorder, comprising administering to the mammal simultaneously or sequentially and in any order: (a) a therapeutically effective amount of one, two or all three of: (i) (R)-fenfluramine or a pharmaceutically acceptable salt, solvate or prodrug thereof, (ii) (R)-norfenfluramine or a pharmaceutically acceptable salt, solvate or prodrug thereof, and (iii) (R)-benfluorex or a pharmaceutically acceptable salt, solvate or prodrug thereof; and (b) a therapeutically effective amount of phentermine, or a pharmaceutically acceptable salt, solvate or prodrug thereof, wherein (R)-fenfluramine is substantially free of (S)-fenfluramine (e.g., greater than 80% ee), (R)-norfenfluramine is substantially free of (S)-norfenfluramine (e.g., greater than 80% ee), and (R)-benfluorex is substantially free of(S)-benfluorex (e.g., greater than 80% ee).

In certain further embodiments of the present methods, the epileptic seizure disorder is Dravet syndrome. In certain other further embodiments of the present methods, the epileptic seizure disorder is selected from photosensitive epilepsy, self-induced syncope, intractable epilepsy, Angelman syndrome, benign rolandic epilepsy, CDKL5 disorder, childhood and juvenile absence epilepsy, Dravet syndrome, frontal lobe epilepsy, Glut1 deficiency syndrome, hypothalamic hamartoma, infantile spasms/West's syndrome, juvenile myoclonic epilepsy, Landau-Kleffner syndrome, Lennox-Gastaut syndrome (LGS), epilepsy with myoclonic-absences, Ohtahara syndrome, Panayiotopoulos syndrome, PCDH19 epilepsy, progressive myoclonic epilepsies, Rasmussen's syndrome, ring chromosome 20 syndrome, reflex epilepsies, temporal lobe epilepsy, Lafora progressive myoclonus epilepsy, neurocutaneous syndromes, tuberous sclerosis complex, early infantile epileptic encephalopathy, early onset epileptic encephalopathy, generalized epilepsy with febrile seizures plus (GEFS+), Rett syndrome, multiple sclerosis, Alzheimer's disease, autism, ataxia, hypotonia, paroxysmal dyskinesia, focal onset seizures, generalized onset seizures, absence seizures, Jeavon Syndrome, epileptic encephalopathy, sunflower syndrome, fragile-X syndrome, alternating hemiplegia, autosomal dominant nocturnal frontal lobe epilepsy (ADNFLE), benign rolandic epilepsy, Doose Syndrome, early myoclonic encephalopathy, epilepsy of infancy with migrating focal seizures, epilepsy with generalized tonic-clonic seizures, epilepsy with myoclonic absences, epileptic encephalopathy with continuous spike and wave during sleep, juvenile absence seizures, progressive myoclonic epilepsies, SCN8A related epilepsy, SCN2A related epilepsy, KCNQ2 related epilepsy, and TBC1 Domain Containing Kinase (TBCK) related intellectual disability (ID) syndrome.

In certain other embodiments, there is provided a method of treating a mammal having or at risk for having an epileptic seizure disorder, comprising administering to the mammal a therapeutically effective amount of racemic norfenfluramine [(R/S)-1-(3-(trifluoromethyl)phenyl)propan-2-amine] or a prodrug thereof.

In certain embodiments, there is provided a method of treating a mammal having or at risk for having an epileptic seizure disorder, comprising administering to the mammal simultaneously or sequentially and in any order: (a) a therapeutically effective amount of racemic norfenfluramine [(R/S)-1-(3-(trifluoromethyl)phenyl)propan-2-amine] or a prodrug thereof; and (b) a therapeutically effective amount of phentermine, or a pharmaceutically acceptable salt, solvate or prodrug thereof.

In certain further embodiments, the epileptic seizure disorder is Dravet syndrome. In certain embodiments the epileptic seizure disorder is selected from photosensitive epilepsy, self-induced syncope, intractable epilepsy, Angelman syndrome, benign rolandic epilepsy, CDKL5 disorder, childhood and juvenile absence epilepsy, Dravet syndrome, frontal lobe epilepsy, Glut1 deficiency syndrome, hypothalamic hamartoma, infantile spasms/West's syndrome, juvenile myoclonic epilepsy, Landau-Kleffner syndrome, Lennox-Gastaut syndrome (LGS), epilepsy with myoclonic-absences, Ohtahara syndrome, Panayiotopoulos syndrome, PCDH19 epilepsy, progressive myoclonic epilepsies, Rasmussen's syndrome, ring chromosome 20 syndrome, reflex epilepsies, temporal lobe epilepsy, Lafora progressive myoclonus epilepsy, neurocutaneous syndromes, tuberous sclerosis complex, early infantile epileptic encephalopathy, early onset epileptic encephalopathy, generalized epilepsy with febrile seizures plus (GEFS+), Rett syndrome, multiple sclerosis, Alzheimer's disease, autism, ataxia, hypotonia, paroxysmal dyskinesia, focal onset seizures, generalized onset seizures, absence seizures, Jeavon Syndrome, epileptic encephalopathy, sunflower syndrome, fragile-X syndrome, alternating hemiplegia, autosomal dominant nocturnal frontal lobe epilepsy (ADNFLE), benign rolandic epilepsy, Doose Syndrome, early myoclonic encephalopathy, epilepsy of infancy with migrating focal seizures, epilepsy with generalized tonic-clonic seizures, epilepsy with myoclonic absences, epileptic encephalopathy with continuous spike and wave during sleep, juvenile absence seizures, progressive myoclonic epilepsies, SCN8A related epilepsy, SCN2A related epilepsy, KCNQ2 related epilepsy, and TBC1 Domain Containing Kinase (TBCK) related intellectual disability (ID) syndrome.

In some embodiments, the present disclosure provides a method of treating epilepsy or an epileptic seizure disorder, comprising administering to a human subject in need thereof a therapeutically effective amount of (R)-fenfluramine or a pharmaceutically acceptable salt thereof, wherein the (R)- fenfluramine or pharmaceutically acceptable salt thereof has an enantiomeric excess (ee) greater than 80, for example greater than 90%, 95%, 97%, 98%, 99%, or 99.5%, or such as an ee between 80% and 99% or 90% and 99%. In certain embodiments, said method of treating epilepsy or an epileptic seizure disorder with an enantiomeric excess of (R)-fenfluramine or a pharmaceutically acceptable salt thereof reduces the frequency of epileptic seizures, such as by reducing seizure frequency or mean convulsive seizure frequency from baseline by at least 20%, such as by at least 25, 35, 50, 60, 65, 70, 75, or 80% from baseline, particularly by at least 25, 50, or 75% from baseline.

In certain embodiments, the present disclosure provides a pharmaceutical composition comprising (R)-fenfluramine or a pharmaceutically acceptable salt thereof and one or more pharmaceutically acceptable excipients, wherein the (R)-fenfluramine or pharmaceutically acceptable salt thereof has an ee greater than 80%, for example greater than 90%, 95%, 97%, 98%, 99%, or 99.5%, or such as an ee between 80% and 99% or 90% and 99%.

In some embodiments, the present disclosure provides a method of treating epilepsy or an epileptic seizure disorder, comprising administering to a human subject in need thereof a therapeutically effective amount of (R)-norfenfluramine or a pharmaceutically acceptable salt or prodrug thereof, wherein the (R)-norfenfluramine or pharmaceutically acceptable salt or prodrug thereof has an enantiomeric excess ee greater than 80%, for example greater than 90%, 95%, 97%, 98%, 99%, or 99.5%, or such as an ee between 80% and 99% or 90% and 99%. In certain embodiments, said method of treating epilepsy or an epileptic seizure disorder with an enantiomeric excess of (R)-norfenfluramine or a pharmaceutically acceptable salt or prodrug thereof reduces the frequency of epileptic seizures, such as by reducing seizure frequency or mean convulsive seizure frequency from baseline by at least 20%, such as by at least 25, 35, 50, 60, 65, 70, 75, or 80% from baseline, particularly by at least 25, 50, or 75% from baseline.

In certain embodiments, the present disclosure provides a pharmaceutical composition comprising (R)-norfenfluramine or a pharmaceutically acceptable salt or prodrug thereof and one or more pharmaceutically acceptable excipients, wherein the (R)-norfenfluramine or pharmaceutically acceptable salt or prodrug thereof has an ee greater than 80%, for example greater than 90%, 95%, 97%, 98%, 99%, or 99.5%, or such as an ee between 80% and 99% or 90% and 99%.

In some embodiments, the present disclosure provides a method of treating epilepsy or an epileptic seizure disorder, comprising administering to a human subject in need thereof a therapeutically effective amount of (R)-benfluorex or a pharmaceutically acceptable salt thereof, wherein the (R)-benfluorex or pharmaceutically acceptable salt thereof has an enantiomeric excess ee greater than 80%, for example greater than 90%, 95%, 97%, 98%, 99%, or 99.5%, or such as an ee between 80% and 99% or 90% and 99%. In certain embodiments, said method of treating epilepsy or an epileptic seizure disorder with an enantiomeric excess of (R)-benfluorex or a pharmaceutically acceptable salt thereof reduces the frequency of epileptic seizures, such as by reducing seizure frequency or mean convulsive seizure frequency from baseline by at least 20%, such as by at least 25, 35, 50, 60, 65, 70, 75, or 80% from baseline, particularly by at least 25, 50, or 75% from baseline.

In certain embodiments, the present disclosure provides a pharmaceutical composition comprising (R)-benfluorex or a pharmaceutically acceptable salt thereof and one or more pharmaceutically acceptable excipients, wherein the (R)-benfluorex or pharmaceutically acceptable salt thereof has an ee greater than 80%, for example greater than 90%, 95%, 97%, 98%, 99%, or 99.5%, such as an ee between 80% and 99% or 90% and 99%, or such as an ee between 80% and 99% or 90% and 99%.

In some embodiments, the present disclosure provides a method of treating epilepsy or an epileptic seizure disorder, comprising administering to a human subject in need thereof a therapeutically effective amount of racemic norfenfluramine or a pharmaceutically acceptable salt or prodrug thereof. In some embodiments, the present disclosure provides racemic norfenfluramine or a pharmaceutically acceptable salt or prodrug thereof for use in treatment, such as in treating epilepsy or an epileptic seizure disorder in a human subject. In certain embodiments, said method of treating epilepsy or an epileptic seizure disorder with racemic norfenfluramine or a pharmaceutically acceptable salt or prodrug thereof reduces the frequency of epileptic seizures, such as by reducing seizure frequency or mean convulsive seizure frequency from baseline by at least 20%, such as by at least 25, 35, 50, 60, 65, 70, 75, or 80% from baseline, particularly by at least 25, 50, or 75% from baseline.

In certain embodiments, the present disclosure provides a pharmaceutical composition comprising racemic norfenfluramine or a pharmaceutically acceptable salt or prodrug thereof and one or more pharmaceutically acceptable excipients. In certain embodiments, the pharmaceutical composition is for use in treatment, such as in treating epilepsy or an epileptic seizure disorder in a human subject.

In some embodiments, the present disclosure provides a compound selected from (R)-fenfluramine or a pharmaceutically acceptable salt thereof, (R)-norfenfluramine or a pharmaceutically acceptable salt or prodrug thereof, and (R)-benfluorex or a pharmaceutically acceptable salt thereof for use in therapy, such as in treating epilepsy or an epileptic seizure disorder in a human subject, wherein the compound has an ee greater than 80%, for example greater than 90%, 95%, 97%, 98%, 99%, or 99.5%, or such as an ee between 80% and 99% or 90% and 99%.

In certain embodiments, the present disclosure provides a pharmaceutical composition comprising a compound and one or more pharmaceutically acceptable excipients, wherein the compound is selected from (R)-fenfluramine or a pharmaceutically acceptable salt thereof, (R)-norfenfluramine or a pharmaceutically acceptable salt or prodrug thereof, and (R)-benfluorex or a pharmaceutically acceptable salt thereof for use in treatment, such as in treating epilepsy or an epileptic seizure disorder in a human subject, wherein the compound has an ee greater than 80%, for example greater than 90%, 95%, 97%, 98%, 99%, or 99.5%, or such as an ee between 80% and 99% or 90% and 99%.

These and other aspects and embodiments of the present disclosure will be evident upon reference to the following detailed description and attached drawings. All of the U.S. patents, U.S. patent application publications, U.S. patent applications, foreign (non-U.S.) patents, foreign (non-U.S.) patent applications and non-patent publications referred to in this specification and/or listed in the Application Data Sheet are incorporated herein by reference in their entirety, as if each was incorporated individually. Aspects and embodiments of the present disclosure can be modified, if necessary, to employ concepts of the various patents, applications and publications to provide yet further embodiments.

4. BRIEF DESCRIPTION OF THE FIGURES

FIG. 1 shows the results of testing candidate AED compounds in the 6 Hz seizure assay in CF-1 mice. Bars represent the percentage of mice protected after IP administration of racemic fenfluramine, (R)-fenfluramine, racemic norfenfluramine, and (R)-norfenfluramine at 20 mg/kg, or vehicle control, one hour before the in vivo assay (n=16 per group).

Figure 2:
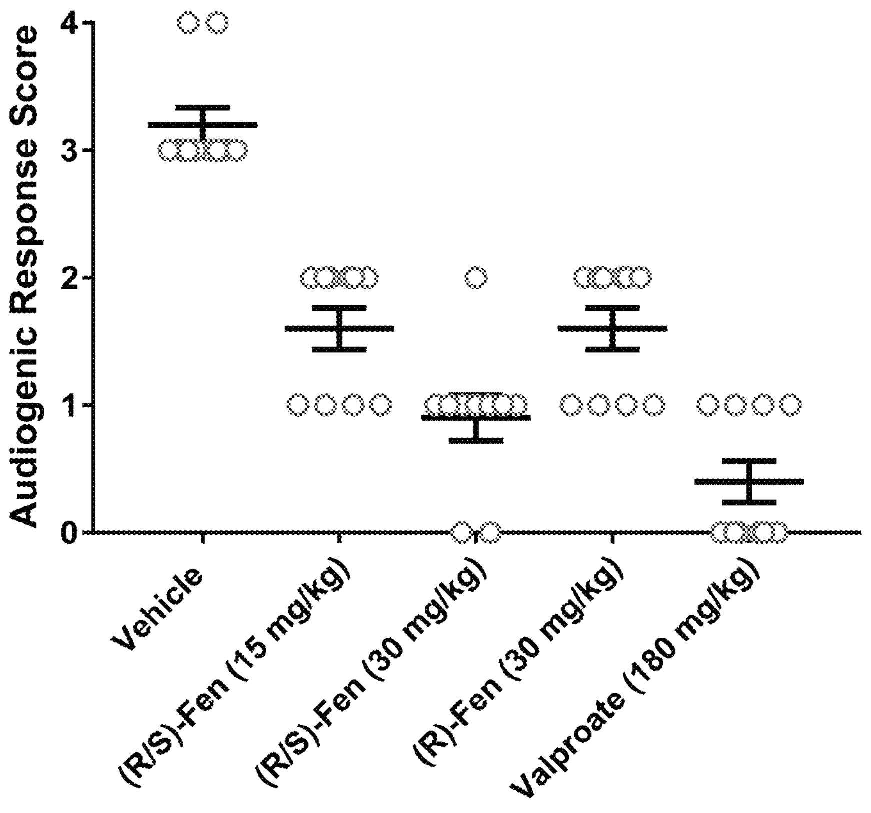

FIG. 2 shows the results of the anticonvulsant effects of (R/S)-fenfluramine and (R)-fenfluramine in the mouse audiogenic seizure test utilizing male DBA/2 mice (n=10/group). Audiogenic response score was assigned as 0 (no seizure), 1 (wild running), 2 (clonic convulsion), 3 (tonic extension), or 4 (death). Results are expressed as mean±SEM with each individual data point shown.

5. DETAILED DESCRIPTION

5.1. Definitions

As used in the specification and appended claims, unless specified to the contrary, the following terms have the meaning indicated:

"Enantiomers" refers to asymmetric molecules that can exist in two different isomeric forms which have different configurations in space. Other terms used to designate or refer to enantiomers include "stereoisomers" (because of the different arrangement or stereochemistry around the chiral center; although all enantiomers are stereoisomers, not all stereoisomers are enantiomers) or "optical isomers" (because of the optical activity of enantiomers, which is the ability of different enantiomers to rotate plane-polarized light in different directions). Because they do not have a plane of symmetry, enantiomers are not identical with their mirror images; molecules which exist in two enantiomeric forms are chiral, which means that they can be regarded as occurring in "left" and "right" handed forms. The most common cause of chirality in organic molecules is the presence of a tetrahedral carbon bonded to four different substituents or groups. Such a carbon is referred to as a chiral center or stereogenic center. A method for indicating the three-dimensional arrangement of atoms (or the configuration) at a stereogenic center is to refer to the arrangement of the priority of the groups when the lowest priority group is oriented away from a hypothetical observer: If the arrangement of the remaining three groups from the higher to the lower priority is clockwise, the stereogenic center has an "R" configuration; if the arrangement is counterclockwise, the stereogenic center has an "S" configuration.

Enantiomers have the same empirical chemical formula, and are generally chemically identical in their reactions, their physical properties, and their spectroscopic properties. However, enantiomers may show different chemical reactivity toward other asymmetric compounds, and may respond differently toward asymmetric physical disturbances. The most common asymmetric disturbance is polarized light.

An enantiomer can rotate plane-polarized light; thus, an enantiomer is optically active. Two different enantiomers of the same compound will rotate plane-polarized light in the opposite direction; thus, the light can be rotated to the left or counterclockwise for a hypothetical observer (this is levorotatory or "l" or minus or "−") or it can be rotated to the right or clockwise (this is dextrorotatory or "d" or plus or "+"). The sign of optical rotation (+) or (−), is not related to the R or S designation. A mixture of equal amounts of two chiral enantiomers is called a racemic mixture, or racemate, and is denoted either by the symbol (+/−) or by the prefix "d/l" to indicate a mixture of dextrorotatory and levorotatory forms. Racemates or racemic mixtures show zero optical rotation because equal amounts of the (+) and (−) forms are present. In general, the presence of a single enantiomer rotates polarized light in only one direction; thus, a single enantiomer is referred to as optically pure.

The designations "R" and "S" are used to denote the absolute configuration of the molecule about its chiral center(s). The designations may appear as a prefix or as a suffix; they may or may not be separated from the enantiomer name by a hyphen; they may or may not be hyphenated; and they may or may not be surrounded by parentheses.

"Resolution" or "resolving" when used in reference to a racemic compound or mixture refers to the separation of a racemate into its two enantiomeric forms (i.e., (+) and (−); (R) and (S) forms).

"Enantiomeric excess" or "ee" refers to a product wherein one enantiomer is present in excess of the other, and is defined as the absolute difference in the mole fraction of each enantiomer. Enantiomeric excess is typically expressed as a percentage of an enantiomer present in a mixture relative to the other enantiomer. For purposes of this disclosure, the (R) enantiomer of a subject compound is considered to be "substantially free" of the (S) enantiomer when the (R) enantiomer is present in enantiomeric excess of greater than 80%, preferably greater than 90%, more preferably greater than 95% and most preferably greater than 99%.

The chemical naming protocol and structure diagrams used herein are a modified form of the IUPAC nomenclature system, using the ACD/Name Version 9.07 software program. For example, the (R)-enantiomer of norfenfluramine, has the following structure:

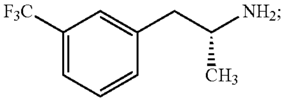

and has a chemical name of (R)-1-(3-(trifluoromethyl)phenyl)propan-2-amine.

"Prodrug" is meant to indicate a compound that may be converted by physiological conditions or by solvolysis to a biologically active compound of the present disclosure. Thus, the term "prodrug" refers to a metabolic precursor of a compound of the present disclosure that is pharmaceutically acceptable. A prodrug may be inactive when administered to a subject in need thereof, but is converted in vivo to an active compound of the present disclosure. Prodrugs are typically rapidly transformed in vivo to yield a compound of the present disclosure, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi et al., "Pro-drugs as Novel Delivery Systems," A.C.S. Symposium Series, Vol. 14, and in Bioreversible Carriers in Drug Design, Ed. Edward B. Roche, American Pharmaceutical Association and Pergamon Press, 1987, both of which are incorporated in full by reference herein.

The term "prodrug" is also meant to include any covalently bonded carriers, which release the active compound of the present disclosure in vivo when such prodrug is administered to a mammalian subject. Prodrugs of a compound of the present disclosure may contain functional groups, which when cleaved by in vivo processes, provide a compound of the present disclosure. Prodrugs include compounds of the present disclosure wherein a hydroxyl, amino or mercapto group is bonded to any group that, when the prodrug is administered to a mammalian subject, cleaves to form a free hydroxyl, free amino or free mercapto group, respectively. Examples of prodrugs include, but are not limited to, acetate, formate and benzoate derivatives of alcohol or amide derivatives of amine functional groups in the compounds of the present disclosure and the like.

For purposes of this disclosure, (R)-fenfluramine and (R)-benfluorex are both considered prodrugs of (R)-norfenfluramine in that both (R)-fenfluramine and (R)-benfluorex metabolize in vivo to (R)-norfenfluramine, which demonstrates the desired anti-epileptic activity of the methods and uses according to certain embodiments described herein.

The present disclosure is also meant to encompass the (R)-enantiomers of the subject compounds being isotopically-labelled by having one or more atoms replaced by an atom having a different atomic mass or mass number. Examples of isotopes that can be incorporated into the disclosed compounds include isotopes of hydrogen, carbon, nitrogen, oxygen, such as $^{2}H$, $^{3}H$, $^{11}C$, $^{13}C$, $^{14}C$, $^{13}N$, $^{15}N$, $^{15}O$, $^{17}O$, $^{18}O$, and $^{18}F$, respectively. These radiolabelled compounds could be useful to help determine or measure the effectiveness of the enantiomers of the subject compounds, by characterizing, for example, the mechanism of action, or binding affinity to pharmacologically important site of action. Isotopically-labelled compounds are useful in drug and/or substrate tissue distribution studies. The radioactive isotopes tritium, i.e., $^{3}H$, and carbon-14, i.e., $^{14}C$, are particularly useful for this purpose in view of their ease of incorporation and ready means of detection. A radioligand incorporating tritium ($^{3}H$) is particularly useful for ligand binding studies with membranes because tritium has a long half-life of decay and the emission is of relatively low energy and the radioisotope is therefore relatively safe. The radioligand is typically prepared by exchange of tritium with a hydrogen in an unlabeled compound.

Substitution with heavier isotopes such as deuterium, i.e., $^{2}H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled enantiomers of the subject compounds can generally be prepared by conventional techniques known to those skilled in the art or by processes analogous to those described herein using an appropriate isotopically-labeled reagent in place of the non-labeled reagent previously employed.

The present disclosure is also meant to encompass the in vivo metabolic products of the disclosed (R)-enantiomers. Such products may result from, for example, the oxidation, reduction, hydrolysis, amidation, esterification, and the like of the administered compound, primarily due to enzymatic processes. Accordingly, the present disclosure includes metabolic products produced by a process comprising contacting an enantiomer of the subject compounds with a mammal for a period of time sufficient to yield the metabolic product. Such metabolic products may be identified by administering a radiolabelled enantiomer of the subject compounds in a detectable dose to an animal, such as a rat, mouse, guinea pig, monkey, or human, allowing sufficient time for metabolism to occur, and isolating the metabolic product from the urine, blood or other biological samples.

"Selectivity" and "selective" as used herein is a relative measure of the tendency for a compound of the present disclosure to preferentially (e.g., in a statistically significant manner) associate with one thing as opposed to another (or group of others).

"Stable enantiomer" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets, (e.g., cats, dogs, swine, cattle, sheep, goats, horses, and rabbits), and non-domestic animals such as wildlife and the like.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier that is suitable for use in humans or domestic animals. Preferably, the carrier, diluent or excipient has been approved by a regulatory agency, for non-limiting example, the United States Food and Drug Administration, Health Canada or the European Medicines Agency, as being acceptable for human or animal pharmaceutical use.

A "pharmaceutical composition" refers to a formulation of a compound of the present disclosure and a medium generally accepted in the art for the delivery of the biologically active compound to mammals, e.g., humans. Such a medium includes all pharmaceutically acceptable carriers, diluents or excipients therefor.

The pharmaceutical compositions of the present disclosure comprise one or more pharmaceutically acceptable excipients, which include, but are not limited to, any solvent, adjuvant, bioavailability enhancer, carrier, glidant, sweetening agent, diluent, preservative, dye/colorant, flavor enhancer, surfactant, wetting agent, dispersing agent, suspending agent, stabilizer, isotonic agent, buffer and/or emulsifier. Preferably, the one or more excipients are approved by, for non-limiting example, the United States Food and Drug Administration, Health Canada or the European Medicines Agency, as being acceptable for use in humans or domestic animals.

"Preventing" epilepsy or another epileptic seizure disorder described herein refers to preventing or reducing, in a statistically significant manner (e.g., relative to an appropriate control), the likelihood of occurrence of said disorder from occurring in a mammal, in particular, when such mammal is predisposed to the condition but has not yet been diagnosed as having it.

"Therapeutically effective amount" refers to that amount of a compound of the present disclosure which, when administered, is sufficient to effect treatment, as defined below, of epilepsy or another epileptic seizure disorder in the recipient mammal, preferably a human. The amount of a compound of the present disclosure which constitutes a "therapeutically effective amount" will vary depending on the compound, the epileptic condition and its severity, the manner of administration, and the age of the mammal to be treated, but can be determined routinely by one of ordinary skill in the art having regard to his or her own knowledge and to this disclosure.

"Treating" or "treatment" as used herein refers to the treatment of epilepsy or another epileptic seizure disorder in a mammal, preferably a human, having the disease or condition of interest, and includes, one or more of the following for examples:

(i) inhibiting epilepsy or another epileptic seizure disorder, i.e., arresting its development, e.g., slowing in a statistically significant manner (e.g., relative to an appropriate control) the increase in the severity, duration, or frequency of epileptic seizures or other symptoms of the disorder;

(ii) relieving epilepsy or another epileptic seizure disorder, i.e., causing statistically significant (e.g., relative to an appropriate control) regression of epilepsy; or (iii) relieving the symptoms resulting from epilepsy or another epileptic seizure disorder, e.g., reducing in a statistically significant manner (e.g., relative to an appropriate control) the severity, duration, or frequency of epileptic seizures or other symptoms of the disorder.

In certain embodiments, treatment with one or more of the (R)-enantiomers of the subject compounds as described herein includes reducing the frequency of epileptic seizures in a statistically significant manner (e.g., relative to an appropriate control), such as reducing seizure frequency or mean convulsive seizure frequency from baseline. In some embodiments, treatment with one or more of the (R)-enantiomers of the subject compounds reduces seizure frequency or mean convulsive seizure frequency from baseline by at least 20%, such as by at least 25, 35, 50, 60, 65, 70, 75, or 80% from baseline, particularly by at least 25, 50, or 75% from baseline.

As used herein, the terms “ameliorating”, “ameliorated”, “alleviating” or “alleviated” are to be given their generally acceptable definitions. For example, to “ameliorate” generally means to make better or to improve a condition relative to the condition prior to the ameliorating event. To “alleviate” generally means to make a condition more bearable relative to the condition prior to the alleviating event. As used herein, “ameliorating” or “ameliorated” can refer to epilepsy or another epileptic seizure disorder or conditions of epilepsy or the epileptic seizure disorder that are made better or improved by the administration of a compound according to the herein disclosed embodiments. As used herein, “alleviating” or “alleviated” can refer to epilepsy or another epileptic seizure disorder or a condition of epilepsy or such other epileptic seizure disorder that is made bearable by the administration of a compound according to the embodiments disclosed herein. For example, “alleviating” epilepsy seizures would include reducing (e.g., decreasing in a statistically significant manner) the severity or incidence of epileptic seizures.

5.2. (R)-Enantiomers of the Present Disclosure

The (R)-enantiomers of the subject compounds of the present disclosure are the (R)-enantiomer of fenfluramine, the (R)-enantiomer of benfluorex and the (R)-enantiomer of norfenfluramine, including the (R)-enantiomers having various enantiomeric excesses as described herein, as well as their pharmaceutically acceptable salts, solvates or prodrugs thereof.

Fenfluramine, which is a racemic mixture of two enantiomers, has the following structure:

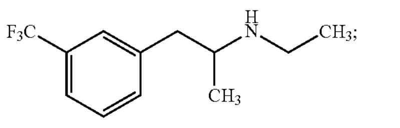

fenfluramine and has a chemical name of (R/S)—N-ethyl-1-(3-(trifluoromethyl)phenyl)propan-2-amine. The preparation of fenfluramine was first disclosed in the French Patent M1658 (1963). The (R)-enantiomer and (S)-enantiomer of fenfluramine have the following structures, respectively:

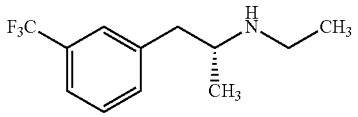

(R)-fenfluramine and

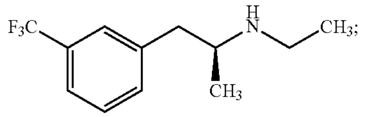

(S)-fenfluramine and respective chemical names of (R)—N-ethyl-1-(3-(trifluoromethyl)phenyl)propan-2-amine and (S)—N-ethyl-1-(3-(trifluoromethyl)phenyl)propan-2-amine.

For purposes of the present disclosure, the (R)-enantiomer of fenfluramine is identified herein as (R)-fenfluramine and the (S)-enantiomer of fenfluramine is identified herein as (S)-fenfluramine. It is understood in the art that (R)-fenfluramine corresponds to levofenfluramine, l-fenfluramine, or (−)-fenfluramine and that (S)-fenfluramine corresponds to dexfenfluramine, d-fenfluramine, or (+)-fenfluramine.

Benfluorex, which is a racemic mixture of two enantiomers, has the following structure:

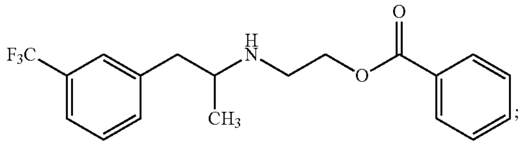

benfluorex and the chemical name of (R/S)-2-(1-(3-(trifluoromethyl)phenyl)propan-2-ylamino)ethyl benzoate. The preparation of benfluorex is described in U.S. Pat. No. 3,607,909.

The (R)-enantiomer and the (S)-enantiomer of benfluorex have the following respective structures:

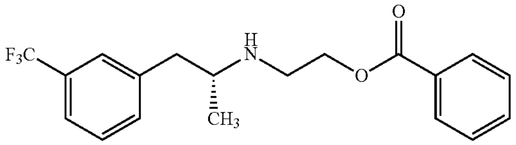

(R)-benfluorex and

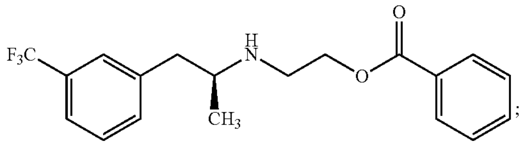

(S)-benfluorex and the respective chemical names of (R)-2-(1-(3-(trifluoromethyl)phenyl)propan-2-ylamino)ethyl benzoate and (S)-2-(1-(3-(trifluoromethyl)phenyl)propan-2-ylamino)ethyl benzoate. For purposes of the present disclosure, the (R)-enantiomer of benfluorex is identified herein as (R)-benfluorex and the (S)-enantiomer of benfluorex is identified herein as (S)-benfluorex.

The active metabolite of both fenfluramine and benfluorex is norfenfluramine, which is also a racemic mixture of two enantiomers. Norfenfluramine has the following structure:

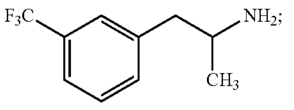

norfenfluramine and a chemical name of (R/S)-1-(3-(trifluoromethyl)phenyl)propan-2-amine. Norfenfluramine racemate (CAS Registry No. [1886-26-6]) is available commercially (e.g., from Toronto Research Chemicals, North York, Ontario, Canada; Clearsynth, Mississauga, Ontario, Canada; or DrugImpurities, North Harrow, UK. The enantiomers of norfenfluramine may be isolated by standard resolution techniques known to one skilled in the art, or can be prepared according to methods known to one skilled in the art or by the methods disclosed herein.

The (R)-enantiomer and the (S)-enantiomer of norfenfluramine have the following respective structures:

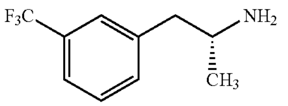

(R)-norfenfluramine and

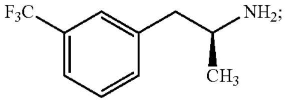

(S)-norfenfluramine and the respective chemical names of (R)-1-(3-(trifluoromethyl)phenyl)propan-2-amine and (R)-1-(3-(trifluoromethyl)phenyl)propan-2-amine. For purposes of the present disclosure, the (R)-enantiomer of norfenfluramine is identified herein as (R)-norfenfluramine and the (S)-enantiomer of norfenfluramine is identified herein as (S)-norfenfluramine. It is understood in the art that (R)-norfenfluramine corresponds to 1-norfenfluramine, or (−)-norfenfluramine and that (S)-norfenfluramine corresponds to d-norfenfluramine, or (+)-norfenfluramine.

In certain embodiments, the (R)-enantiomers of the subject compounds (i.e., one or more of fenfluramine, benfluorex, and/or norfenfluramine) are employed in the methods, uses, and compositions as described herein in enantiomeric excess (ee), such as with an ee greater than 20%, 30%, 40%, 50%, 60%, 70%, 80%, 85%, 90%, 95%, 96%, 97%, 98%, 99%, or 99.5%. In some embodiments, the (R)-enantiomers of the subject compounds are employed in the methods, uses, and compositions as described herein with an ee between 20% to 97%, 98%, or 99%, such as between 30% to 99%, 40% to 99%, 50% to 99%, 60% to 99%, 70% to 99%, 80% to 99%, 85% to 99%, 90% to 99%, 95% to 99%, 96% to 99%, or 97% to 99%, particularly 90% to 99%.

5.3. Utility and Testing of the Compounds of the Present Disclosure

The present disclosure relates, in certain preferred embodiments, to methods of using or the use of the (R)-enantiomers of the subject compounds (i.e., one or more of fenfluramine, benfluorex, and/or norfenfluramine), and pharmaceutical compositions comprising same for the treatment or prevention as provided herein of epilepsy or another epileptic seizure disorder.

The presently disclosed embodiments are based in part on the unexpected and previously unpredictable discoveries (i) that the (R)-enantiomers of the subject compounds possess multiple specific beneficial activities of fenfluramine (or its metabolite norfenfluramine), and are thus therapeutically effective for the treatment or prevention as provided herein of an epileptic seizure disorder, and (ii) that such therapeutically effective (R)-enantiomers can be prepared in a form substantially free (e.g., greater than 80% ee) of the corresponding (S)-enantiomers, in which resides the specific deleterious activity of fenfluramine (or its metabolite norfenfluramine) that undesirably contributes to the harmful cardiotoxicity of fenfluramine.

Specifically, it is disclosed herein for the first time that desirable anti-seizure activities of fenfluramine reside in (R)-fenfluramine or its metabolite, (R)-norfenfluramine, and that these specific enantiomers possess only low levels of undesirable fenfluramine cardiotoxic activity and so are effective AEDs. Conversely, the bulk of fenfluramine cardiotoxic activity resides in (S)-fenfluramine or its metabolite, (S)-norfenfluramine, and these enantiomers are therefore unsuitable as candidate AEDs. As also described herein, by providing the (R)-enantiomers of the subject compounds substantially free (e.g., greater than 80% ee) of the corresponding (S)-enantiomers, AED pharmaceutical compositions, methods, and uses are disclosed for the first time that provide therapeutically beneficial fenfluramine effects for the treatment or prevention (as provided herein) of epileptic seizure disorders while substantially avoiding the harmful cardiotoxicity associated with fenfluramine and norfenfluramine.

Still more specifically, the undesirable cardiotoxicity of fenfluramine resides in serotonin receptor 2B agonist activity (5-HT2B receptor agonist activity), which segregates predominantly with (S)-fenfluramine and its metabolite (S)-norfenfluramine. Hence, preparation of (R)-fenfluramine that is substantially free (e.g., greater than 80% ee) of (S)-fenfluramine surprisingly results in an enantiomerically-enriched preparation characterized by significantly lower cardiotoxic effects relative to a preparation prepared from (S)-fenfluramine, (S)-norfenfluramine, fenfluramine or norfenfluramine, thereby providing a useful AED.

Additionally, preparation of (R)-fenfluramine that is substantially free (e.g., greater than 80% ee) of (S)-fenfluramine surprisingly results in an enantiomeric AED composition that possesses serotonin receptor 2A (5-HT2A receptor) agonist activity and also serotonin receptor 2C (5-HT2C receptor) agonist activity, and that can be metabolized to (R)-norfenfluramine, which exhibits enhanced 5-HT2A/5-HT2C agonist activity along with the desirable AED property of promoting norepinephrine (NE) release. According to non-limiting theory, for certain embodiments, an AED has the following activity profile: 5-HT2A agonist/5-HT2C agonist/NE release promoter/poor 5-HT2B agonist. As disclosed herein, (R)-fenfluramine and its metabolite (R)-norfenfluramine unexpectedly exhibit this preferred profile to provide an unprecedented candidate AED for use in the present methods.

Prior to the present disclosure, it was appreciated in the art that potent 5-HT2A agonist activity, potent 5-HT2C agonist activity, and potent NE release-promoting activity, were all present in (S)-norfenfluramine, which would therefore have been regarded as a candidate AED. Because (S)-norfenfluramine also exhibits potent 5-HT2B agonist activity, however, it would also have been regarded as a source of undesirable fenfluramine cardiotoxicity that could not be separated from desirably potent fenfluramine AED activities. (Rothman et al., *Pharmacol. Biochem. Behav.* 71:825 (2002); Rothman et al., *J. Pharmacol. Exp. Therapeut.* 305:1191 (2003)).

The present disclosure for the first time teaches that a therapeutically effective AED may be obtained by selection of the less potent (R)-fenfluramine, despite the fact that (R)-fenfluramine and its metabolite (R)-norfenfluramine exhibit suboptimal 5-HT2A agonist and NE release promoter activities (i.e., activities that are less potent than for (S)-fenfluramine and (S)-norfenfluramine, respectively). Without wishing to be bound by theory, the present selection of the less potent (R)-fenfluramine or (R)-norfenfluramine as an AED for treating or preventing (as provided herein) an epileptic seizure disorder provides therapeutic efficacy so long as the (R)-enantiomers are also poor 5-HT2B agonists relative to fenfluramine or norfenfluramine. Accordingly, the advantages associated with selecting (R)-fenfluramine and (R)-norfenfluramine for use in the present methods of treating or preventing (as provided herein) an epileptic seizure disorder would not have been predicted prior to the present disclosure, where the suitability of these enantiomers as AEDs had not previously been recognized.

The present disclosure is therefore directed, in certain embodiments, to methods of treating a mammal, preferably a human, having or at risk for having an epileptic seizure disorder, comprising administering to the mammal a therapeutically effective amount of one, two or all three of:

(i) (R)-fenfluramine or a pharmaceutically acceptable salt, solvate or prodrug thereof, (ii) (R)-norfenfluramine or a pharmaceutically acceptable salt, solvate or prodrug thereof, and (iii) (R)-benfluorex or a pharmaceutically acceptable salt, solvate or prodrug thereof, wherein (R)-fenfluramine is substantially free of (S)-fenfluramine (e.g., greater than 80% ee), (R)-norfenfluramine is substantially free of (S)-norfenfluramine (e.g., greater than 80% ee), and (R)-benfluorex is substantially free of (S)-benfluorex (e.g., greater than 80% ee).

The present disclosure is likewise directed to the use of one, two or all three of the above compounds—(i), (ii), and (iii)—for treating a mammal, preferably a human, having or at risk for having an epileptic seizure disorder.

In certain other embodiments, the present disclosure is directed to a method of treating a mammal having or at risk for having an epileptic seizure disorder, comprising administering to the mammal a therapeutically effective amount of racemic norfenfluramine [(R/S)-1-(3-(trifluoromethyl)phenyl)propan-2-amine]. The present disclosure is also directed to the use of racemic norfenfluramine for treating a mammal having or at risk for having an epileptic seizure disorder.

In some embodiments, the present disclosure is directed to one, two or all three of the above compounds—(i), (ii), and (iii)—or racemic norfenfluramine for use in therapy.

5.3.1. Epilepsy and Epileptic Seizure Disorders

The methods and uses of the present disclosure, in some embodiments, are directed to the treatment of mammals, preferably humans, for epilepsy. In particular embodiments, the methods and uses of the present disclosure are directed to the treatment of mammals, preferably humans, having or at risk for having an epileptic seizure disorder.

Epilepsy and epileptic seizure disorders are described above. Persons skilled in the relevant art will be familiar with any number of diagnostic, prognostic, surgical, genetic and/or other clinical criteria for identifying a subject or patient having or being at risk for having epilepsy or any epileptic seizure disorder, as may indicate the clinical appropriateness of, and/or to which can be adapted, administration of the AED compositions described herein. See, e.g., Sontheimer, Diseases of the Nervous System, 2015 Academic Press/Elsevier, Waltham, MA; "Neurologic Disorders" in The Merck Manual of Diagnosis and Therapy 19th Ed. (R. S. Porter, Ed., 2011, Merck, Inc., NJ); "Neurological Diagnostic Tests and Procedures" at the website of the National Institute of Neurological Disorders and Stroke, National Institutes of Health, Bethesda, MD, www.ninds.nih.gov/disorders/misc/diagnostic_tests.htm; Neurology in Clinical Practice—Vol. II, 4th Edition, Bradley et al., (Eds), 2004 Butterworth Heinemann/Elsevier, Philadelphia, PA; Non-Neoplastic Diseases of the Central Nervous System (Atlas of Nontumor Pathology—First Series Fascicle), D. N. Lewis et al., (eds.), 2010 Amer. Registry of Pathology, Annapolis Junction, MD; Bradley's Neurology in Clinical Practice (6th Ed.), R. B. Daroff et al. (eds.), 2012 Saunders/Elsevier, Waltham, MA; see also, e.g., Wright et al., 2016 *Molec. Genet. Genom. Med.* 4(2): 197; Claes et al., 2001 *Am. J. Hum. Genet.* 68:1327-1332; Marini et al., 2011 *Epilepsia* 52(Suppl. 2):24-29; Ceulemans et al., 2012 *Epilepsia* 53(7): 1131-1139). Criteria for diagnosis and clinical monitoring of patients having or suspected of having epilepsy or any other epileptic seizure disorder are thus well known to those skilled in the relevant art.

Accordingly, the herein described compositions and methods are useful in treating or preventing (as provided herein) a wide range of diseases, disorders or conditions that relate to epilepsy or an epileptic seizure disorder, including but not limited to photosensitive epilepsy, self-induced syncope, intractable epilepsy, focal onset epilepsy, Angelman syndrome, benign rolandic epilepsy, CDKL5 disorder, childhood and juvenile absence epilepsy, Dravet syndrome, frontal lobe epilepsy, Glut1 deficiency syndrome, hypothalamic hamartoma, infantile spasms/West's syndrome, juvenile myoclonic epilepsy, Landau-Kleffner syndrome, Lennox-Gastaut syndrome (LGS), epilepsy with myoclonic-absences, Ohtahara syndrome, Panayiotopoulos syndrome, PCDH19 epilepsy, progressive myoclonic epilepsies, Rasmussen's syndrome, ring chromosome 20 syndrome, reflex epilepsies, temporal lobe epilepsy, Lafora progressive myoclonus epilepsy, neurocutaneous syndromes, tuberous sclerosis complex, early infantile epileptic encephalopathy, early onset epileptic encephalopathy, generalized epilepsy with febrile seizures plus (GEFS+), Rett syndrome, multiple sclerosis, Alzheimer's disease, autism, ataxia, hypotonia and paroxysmal dyskinesia.

5.3.2. In Vitro Assays

In vitro assays for determining the efficacy of the (R)-enantiomers as 5HT2C and/or 5HT2A agonists are known. See, for example, Rothman et al., 2003 *J. Pharmacol. Exp.*

*Therapeut.* 305(3): 1191-1199; Lawrence et al., 2000 *Molecular Pharmacology,* 57:75-81; Porter et al., 1999 *Brit. J of Pharmacology* 128:13-20.

5.3.3. Animal Models

Animal models for testing the efficacy of the (R)-enantiomers of the subject compounds in treating or preventing (as provided herein) epilepsy or epileptic seizure disorders are well known. See, for example, the animal models described below in the Biological Examples.

5.3.4. Dosage

Typically, a successful therapeutic agent of certain disclosed embodiments will meet some or all of the following criteria. Oral availability should be at or above 20%. Animal model efficacy is less than about 0.1 μg to about 100 mg/kg body weight and the target human dose is between 0.1 μg to about 100 mg/kg body weight, although doses outside of this range may be acceptable ("mg/kg" means milligrams of compound per kilogram of body mass of the subject to whom it is being administered). The therapeutic index (or ratio of toxic dose to therapeutic dose) should be greater than 100. The potency (e.g., as expressed by IC50 value as determined by in vitro characterization against its target) should be less than 10 μM, preferably below 1 μM and most preferably below 50 nM.

In certain embodiments, the methods and uses disclosed herein include administration of a dose of about 0.1 mg/kg to about 50 mg/kg of an (R)-enantiomer of one or more of the subject compounds, such as fenfluramine, including about 0.25, 0.5, 0.75, 1, 1.5, 2, 2.5, 5, 10, 15, 20, or 25 mg/kg to about 35, 40, 45, or 50 mg/kg, such as about 20 to 40 mg/kg or 25 to 35 mg/kg, such as 20, 25, 30, 35, or 40 mg/kg+/−5%, including 30 mg/kg+/−5%. In certain embodiments, the methods and uses disclosed herein include administration of a dose of about 0.1 mg/kg to about 10 mg/kg of an (R)-enantiomer of one or more of the subject compounds, such as fenfluramine, including about 0.25, 0.5, 0.75, or 1 mg/kg to about 2, 2.5, 5, or 10 mg/kg, such as about 0.5 mg/kg to about 2.5 mg/kg or about 1 mg/kg to about 2 mg/kg, such as 0.5, 0.75, 1, 1.5, 2, 2.25, or 2.5 mg/kg+/−5%, including 1 mg/kg+/−5% or 2 mg/kg+/−5%. In a particular embodiment, a dose of 1 mg/kg to 2 mg/kg is administered to a human subject for treatment of epilepsy or an epileptic seizure disorder, for example Dravet syndrome. In embodiments where more than one of the subject compounds is administered according to the present methods and uses, the above doses can represent the combined total doses of the compounds administered, or the above doses can represent the individual doses of each of the compounds administered.

In some embodiments, the methods and uses disclosed herein include administration of a human dose of an (R)-enantiomer of one or more of the subject compounds, such as fenfluramine, that corresponds to a mouse dose of about 1 mg/kg to about 50 mg/kg, including a mouse dose of about 1, 5, 10, 15, 20, or 25 mg/kg to about 35, 40, 45, or 50 mg/kg, such as about 20 to 40 mg/kg or 25 to 35 mg/kg, such as 20, 25, 30, 35, or 40 mg/kg+/−5%, including 30 mg/kg+/−5%. In embodiments where more than one of the subject compounds is administered according to the present methods and uses, the above doses can represent the combined total doses of the compounds administered, or the above doses can represent the individual doses of each of the compounds administered.

5.4. Pharmaceutical Compositions of the Present Disclosure and Administration The present disclosure also relates in certain embodiments to pharmaceutical compositions comprising the (R)-enantiomers of the subject compounds, including the (R)-enantiomers having various enantiomeric excesses as described herein, and one or more pharmaceutically acceptable excipients. In one embodiment, the present disclosure relates to pharmaceutical compositions comprising the (R)-enantiomers of the subject compounds, individually or in combination thereof, in a pharmaceutically acceptable carrier or excipient and in an amount effective to treat or prevent (as provided herein) epilepsy or another epileptic seizure disorder when administered to an animal, preferably a mammal, most preferably a human patient.

In another embodiment, the present disclosure relates to pharmaceutical compositions comprising a therapeutically effective amount of one, two or all three of:

(i) (R)-fenfluramine or a pharmaceutically acceptable salt, solvate or prodrug thereof;

(ii) (R)-norfenfluramine or a pharmaceutically acceptable salt, solvate or prodrug thereof, and (iii) (R)-benfluorex or a pharmaceutically acceptable salt, solvate or prodrug thereof;

and a pharmaceutically acceptable excipient, wherein (R)-fenfluramine is substantially free of (S)-fenfluramine (e.g., greater than 80% ee), (R)-norfenfluramine is substantially free of (S)-norfenfluramine (e.g., greater than 80% ee), and (R)-benfluorex is substantially free of (S)-benfluorex (e.g., greater than 80% ee).

In some embodiments, the present disclosure relates to a pharmaceutical composition comprising (R)-fenfluramine or a pharmaceutically acceptable salt thereof and one or more pharmaceutically acceptable excipients, wherein the (R)-fenfluramine or pharmaceutically acceptable salt thereof is in enantiomeric excess as described herein, such as having greater than 80%, 90%, 95%, 97%, 98%, 99%, or 99.5% ee. In some embodiments, such a pharmaceutical composition includes an amount of the (R)-fenfluramine or a pharmaceutically acceptable salt thereof that is not 30 mg, i.e., includes an amount that is less than or greater than 30 mg, such as greater than 31, 32, 35, 40, 45, or 50 mg or less than 29, 27, or 25 mg. In certain embodiments, the pharmaceutical composition includes an amount of the (R)-fenfluramine or a pharmaceutically acceptable salt thereof from 31, 32, 35, 40, 45, or 50 mg to 100, 150, 200, 250, 300, 350, or 400 mg, such as 31 mg to 150 mg, 32 mg to 150 mg, 35 mg to 150 mg, 40 mg to 150 mg, 50 mg to 150 mg, 31 mg to 200 mg, 32 mg to 200 mg, 35 mg to 200 mg, 40 mg to 200 mg, 50 mg to 200 mg, 31 mg to 300 mg, 32 mg to 300 mg, 35 mg to 300 mg, 40 mg to 300 mg, 50 mg to 300 mg, 31 mg to 400 mg, 32 mg to 400 mg, 35 mg to 400 mg, 40 mg to 400 mg, or 50 mg to 400 mg. In some embodiments, the pharmaceutical composition includes an amount of the (R)-fenfluramine or a pharmaceutically acceptable salt thereof from 1, 2, 3, 5, 7, or 10 mg to 25, 27, or 29 mg, such as from 5 mg to 25 mg, 5 mg to 27 mg, 5 mg to 29 mg, 10 mg to 25 mg, 10 mg to 27 mg, or 10 mg to 29 mg. In some instances, the pharmaceutical composition includes an amount of the (R)-fenfluramine or a pharmaceutically acceptable salt thereof from 5, 10, 15, or 20 mg to 100, 150, 200, 250, 300, 350, or 400 mg, such as 10, 15, 20, 25, 30, 35, 40, 45, 50, 60, 75, 80, 100, 125, 150, 175, 200, 225, 250, 300, 350, or 400 mg.

In some embodiments, the present disclosure relates to a pharmaceutical composition comprising (R)-benfluorex or a pharmaceutically acceptable salt thereof and one or more pharmaceutically acceptable excipients, wherein the (R)-benfluorex or pharmaceutically acceptable salt thereof is in enantiomeric excess as described herein, such as having greater than 80%, 90%, 95%, 97%, 98%, 99%, or 99.5% ee. In some embodiments, such a pharmaceutical composition includes an amount of the (R)-benfluorex or a pharmaceutically acceptable salt thereof that is not 30 mg, i.e., includes an amount that is less than or greater than 30 mg, such as greater than 31, 32, 35, 40, 45, or 50 mg or less than 29, 27, or 25 mg. In certain embodiments, the pharmaceutical composition includes an amount of the (R)-benfluorex or a pharmaceutically acceptable salt thereof from 31, 32, 35, 40, 45, or 50 mg to 100, 150, 200, 250, 300, 350, or 400 mg, such as 31 mg to 150 mg, 32 mg to 150 mg, 35 mg to 150 mg, 40 mg to 150 mg, 50 mg to 150 mg, 31 mg to 200 mg, 32 mg to 200 mg, 35 mg to 200 mg, 40 mg to 200 mg, 50 mg to 200 mg, 31 mg to 300 mg, 32 mg to 300 mg, 35 mg to 300 mg, 40 mg to 300 mg, 50 mg to 300 mg, 31 mg to 400 mg, 32 mg to 400 mg, 35 mg to 400 mg, 40 mg to 400 mg, or 50 mg to 400 mg. In some embodiments, the pharmaceutical composition includes an amount of the (R)-benfluorex or a pharmaceutically acceptable salt thereof from 1, 2, 3, 5, 7, or 10 mg to 25, 27, or 29 mg, such as from 5 mg to 25 mg, 5 mg to 27 mg, 5 mg to 29 mg, 10 mg to 25 mg, 10 mg to 27 mg, or 10 mg to 29 mg. In some instances, the pharmaceutical composition includes an amount of the (R)-benfluorex or a pharmaceutically acceptable salt thereof from 5, 10, 15, or 20 mg to 100, 150, 200, 250, 300, 350, or 400 mg, such as 10, 15, 20, 25, 30, 35, 40, 45, 50, 60, 75, 80, 100, 125, 150, 175, 200, 225, 250, 300, 350, or 400 mg.

In some embodiments, the present disclosure relates to a pharmaceutical composition comprising (R)-norfenfluramine or a pharmaceutically acceptable salt or prodrug thereof and one or more pharmaceutically acceptable excipients, wherein the (R)-norfenfluramine or pharmaceutically acceptable salt or prodrug thereof is in enantiomeric excess as described herein, such as having greater than 80%, 90%, 95%, 97%, 98%, 99%, or 99.5% ee. In some embodiments, such a pharmaceutical composition includes an amount of the (R)-norfenfluramine or a pharmaceutically acceptable salt or prodrug thereof that is not 30 mg, i.e., includes an amount that is less than or greater than 30 mg, such as greater than 31, 32, 35, 40, 45, or 50 mg or less than 29, 27, or 25 mg. In certain embodiments, the pharmaceutical composition includes an amount of the (R)-norfenfluramine or a pharmaceutically acceptable salt or prodrug thereof from 31, 32, 35, 40, 45, or 50 mg to 100, 150, 200, 250, 300, 350, or 400 mg, such as 31 mg to 150 mg, 32 mg to 150 mg, 35 mg to 150 mg, 40 mg to 150 mg, 50 mg to 150 mg, 31 mg to 200 mg, 32 mg to 200 mg, 35 mg to 200 mg, 40 mg to 200 mg, 50 mg to 200 mg, 31 mg to 300 mg, 32 mg to 300 mg, 35 mg to 300 mg, 40 mg to 300 mg, 50 mg to 300 mg, 31 mg to 400 mg, 32 mg to 400 mg, 35 mg to 400 mg, 40 mg to 400 mg, or 50 mg to 400 mg. In some embodiments, the pharmaceutical composition includes an amount of the (R)-norfenfluramine or a pharmaceutically acceptable salt or prodrug thereof from 1, 2, 3, 5, 7, or 10 mg to 25, 27, or 29 mg, such as from 5 mg to 25 mg, 5 mg to 27 mg, 5 mg to 29 mg, 10 mg to 25 mg, 10 mg to 27 mg, or 10 mg to 29 mg. In some instances, the pharmaceutical composition includes an amount of the (R)-norfenfluramine or a pharmaceutically acceptable salt or prodrug thereof from 5, 10, 15, or 20 mg to 100, 150, 200, 250, 300, 350, or 400 mg, such as 10, 15, 20, 25, 30, 35, 40, 45, 50, 60, 75, 80, 100, 125, 150, 175, 200, 225, 250, 300, 350, or 400 mg.

In certain embodiments, the present disclosure relates to a pharmaceutical composition that provides an enantiomeric excess of (R)-norfenfluramine or a pharmaceutically acceptable salt or prodrug thereof. In such embodiments, the enantiomeric excess can be as described herein, such as having greater than 80%, 90%, 95%, 97%, 98%, 99%, or 99.5% ee. Such a pharmaceutical composition may include one or more pharmaceutically acceptable excipients as described herein.

In another embodiment, the present disclosure relates to a pharmaceutical composition comprising a therapeutically effective amount of norfenfluramine racemate or a pharmaceutically acceptable salt or prodrug thereof.

Administration of the (R)-enantiomers of the present disclosure (or in certain embodiments norfenfluramine racemate), in pure form or in an appropriate pharmaceutical composition, can be carried out via any of the accepted modes of administration of agents for serving similar utilities. The pharmaceutical compositions of the present disclosure can be prepared by combining a subject compound with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, rectal, vaginal, and intranasal. The term parenteral as used herein includes subcutaneous injections, intravenous, intramuscular, intrasternal injection or infusion techniques. Pharmaceutical compositions of the present disclosure are formulated so as to allow the active ingredients contained therein to be bioavailable upon administration of the composition to a patient. Compositions that will be administered to a subject or patient, preferably a mammal, more preferably a human, may take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see The Science and Practice of Pharmacy, 20th Edition (Philadelphia College of Pharmacy and Science, 2000). The composition to be administered will, in any event, contain a therapeutically effective amount of a subject compound, or a pharmaceutically acceptable salt thereof, for treatment or prevention (as provided herein) of a disease or condition of interest in accordance with the teachings of this disclosure.

The pharmaceutical compositions useful herein also contain a pharmaceutically acceptable carrier, including any suitable diluent or excipient, which includes any pharmaceutical agent that does not itself induce the production of antibodies harmful to the individual receiving the composition, and which may be administered without undue toxicity. Pharmaceutically acceptable carriers include, but are not limited to, liquids, such as water, saline, glycerol and ethanol, and the like. A thorough discussion of pharmaceutically acceptable carriers, diluents, and other excipients is presented in Remington's Pharmaceutical Sciences (Mack Pub. Co., N.J., current edition).

A pharmaceutical composition of the present disclosure may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred compositions contain, in addition to the (R)-enantiomers of the subject compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the present disclosure, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid (EDTA); buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the present disclosure intended for either parenteral or oral administration should contain an amount of an (R)-enantiomer of the subject compounds such that a suitable dosage will be obtained. Typically, this amount of an (R)-enantiomer of the subject compounds is at least 0.01% by the weight of the composition. When intended for oral administration, this amount may be varied to be between 0.1 and about 70% by the weight of the composition. Preferred oral pharmaceutical compositions contain between about 4% to about 50% of an (R)-enantiomer of the subject compounds, such as between about 5%, 7%, 10%, or 15% to about 20%, 25%, 30%, 35%, 40%, or 45%. Preferred pharmaceutical compositions and preparations according to the present disclosure are prepared so that a parenteral dosage unit contains between 0.01 to 10% by weight of the (R)-enantiomer of the subject compounds prior to dilution, such as between 0.01% to 4%, 5%, 6%, 7%, 8%, or 9% by weight prior to dilution, or between 0.01%, 0.2%, 0.5%, 0.8%, 1%, 1.5%, 2%, 3%, 4% or 5% to 10% by weight prior to dilution.

The pharmaceutical composition of the present disclosure may be intended for topical administration, in which case the carrier may suitably comprise a solution, emulsion, ointment or gel base. The base, for example, may comprise one or more of the following: petrolatum, lanolin, polyethylene glycols, beeswax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the (R)-enantiomer of the subject compounds from about 0.1 to about 10% w/v (weight per unit volume), such as between 0.01% to 4%, 5%, 6%, 7%, 8%, or 9% by weight prior to dilution, or between 0.01%, 0.2%, 0.5%, 0.8%, 1%, 1.5%, 2%, 3%, 4% or 5% to 10% by weight prior to dilution.

The pharmaceutical composition of the present disclosure may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

A typical formulation for intramuscular or intrathecal administration will consist of a suspension or solution of active in an oil or solution of active ingredient in an oil, for example arachis oil or sesame oil. A typical formulation for intravenous or intrathecal administration will consist of sterile isotonic aqueous solution containing, for example active ingredient and dextrose or sodium chloride or a mixture of dextrose and sodium chloride. The compositions of the present disclosure can be formulated so as to provide quick, sustained or delayed release of the active ingredient, i.e., the (R)-enantiomer of the subject compounds (or in certain embodiments norfenfluramine racemate), after administration to the patient by employing procedures known in the art. Controlled release drug delivery systems include osmotic pump systems and dissolutional systems containing polymer-coated reservoirs or drug-polymer matrix formulations. Examples of controlled release systems are given in U.S. Pat. Nos. 3,845,770 and 4,326,525 and in P. J. Kuzma et al., *Regional Anesthesia* 1997, 22(6):543-551, all of which are incorporated herein by reference.

The compositions of the present disclosure can also be delivered through intra-nasal drug delivery systems for local, systemic, and nose-to-brain medical therapies. Controlled Particle Dispersion (CPD)™ technology, traditional nasal spray bottles, inhalers or nebulizers are known by those skilled in the art to provide effective local and systemic delivery of drugs by targeting the olfactory region and paranasal sinuses.

The present disclosure also relates to an intravaginal shell or core drug delivery device suitable for administration to the human or animal female. The device may be comprised of the active pharmaceutical ingredient in a polymer matrix, surrounded by a sheath, and capable of releasing the (R)-enantiomer of the subject compounds in a substantially zero order pattern on a daily basis similar to devices used to apply testosterone as described in PCT Published Patent Application No. WO 98/50016 and U.S. Pat. No. 6,416,780.

The most suitable route of administration will depend on the nature and severity of the condition being treated. Those skilled in the art are also familiar with determining administration methods (e.g., oral, intravenous, inhalation, subcutaneous, rectal, etc.), dosage forms, suitable pharmaceutical excipients and other matters relevant to the delivery of an (R)-enantiomer of the subject compounds to a subject in need thereof.

The pharmaceutical composition of the present disclosure may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the present disclosure in solid or liquid form may include an agent that binds to an (R)-enantiomer of the subject compounds and thereby assists in the delivery of the compound. Suitable agents that may act in this capacity include a monoclonal or polyclonal antibody, a protein or a liposome.

The pharmaceutical composition of the present disclosure may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of an (R)-enantiomer of the subject compounds may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the present disclosure may be prepared by methodology well known in the pharmaceutical art. For example, a pharmaceutical composition intended to be administered by injection can be prepared by combining an (R)-enantiomer of the subject compounds (or in certain embodiments, norfenfluramine racemate) with sterile, distilled water so as to form a solution. A surfactant may be added to facilitate the formation of a homogeneous solution or suspension. Surfactants are compounds that non-covalently interact with an (R)-enantiomer of the subject compounds so as to facilitate dissolution or homogeneous suspension of the compound in the aqueous delivery system.

Generally, a therapeutically effective daily dose of an (R)-enantiomer of the subject compounds (or in certain embodiments, norfenfluramine racemate) is (for a 70 kg mammal) from about 0.001 mg/kg (i.e., 0.07 mg) to about 100 mg/kg (i.e., 7.0 g); preferably a therapeutically effective daily dose is (for a 70 kg mammal) from about 0.01 mg/kg (i.e., 0.70 mg) to about 50 mg/kg (i.e., 3.5 g); and more preferably a therapeutically effective daily dose is (for a 70 kg mammal) from about 1 mg/kg (i.e., 70 mg) to about 25 mg/kg (i.e., 1.75 g). In some embodiments, a therapeutically effective daily dose of an (R)-enantiomer of the subject compounds (or in certain embodiments, norfenfluramine racemate) is (for a 70 kg mammal), from about 0.5 mg/kg to about 2.5 mg/kg, such as 0.75 mg/kg to about 2.25 mg/kg, 1 mg/kg to about 2 mg/kg, or about 1 mg/kg or about 2 mg/kg.

The ranges of effective doses provided herein are not intended to be limiting and represent preferred dose ranges. However, the most preferred dosage will be tailored to the individual subject, as is understood and determinable by one skilled in the relevant arts (see, e.g., Berkow et al., eds., The Merck Manual, 19th edition, Merck and Co., Rahway, N.J., 2011; Brunton et al., eds., Goodman and Gilman's The Pharmacological Basis of Therapeutics, 12th edition, McGraw-Hill 2011; Avery's Drug Treatment: Principles and Practice of Clinical Pharmacology and Therapeutics, 3rd edition, ADIS Press, LTD., Williams and Wilkins, Baltimore, MD (1987), Ebadi, Pharmacology, Little, Brown and Co., Boston, (1985); Osolci al., eds., Remington's Pharmaceutical Sciences, current edition, Mack Publishing Co., Easton, PA; Katzung, Basic and Clinical Pharmacology, Appleton and Lange, Norwalk, CT (1992)).

The total dose required for each treatment can be administered by multiple doses or in a single dose over the course of the day, if desired. Generally, treatment is initiated with smaller dosages, which are less than the optimum dose of the compound. Thereafter, the dosage is increased by small increments until the optimum effect under the circumstances is reached. The present pharmaceutical compound or composition can be administered alone or in conjunction with other diagnostics and/or pharmaceuticals directed to the pathology, or directed to other symptoms of the pathology. Effective amounts of the (R)-enantiomer of the subject compounds (or in certain embodiments, norfenfluramine racemate) or pharmaceutical composition of the present disclosure are from about 0.1 μg to about 100 mg/kg body weight, administered at intervals of 4-72 hours, for a period of 2 hours to 1 year, and/or any range or value therein, such as 0.0001-0.001, 0.001-0.01, 0.01-0.1, 0.1-1.0, 1.0-10, 5-10, 10-20, 20-50 and 50-100 mg/kg, at intervals of 1-4, 4-10, 10-16, 16-24, 24-36, 24-36, 36-48, 48-72 hours, for a period of 1-14, 14-28, or 30-44 days, or 1-24 weeks, or any range or value therein.

The recipients of administration of an (R)-enantiomer of the subject compounds (or in certain embodiments, norfenfluramine racemate) and/or pharmaceutical compositions of the present disclosure can be any mammal, including mammals of the Orders Primate (including humans, apes and monkeys), Arteriodactyla (including horses, goats, cows, sheep, pigs), Rodenta (including mice, rats, and hamsters), Lagamorpha (including rabbits) and Carnivora (including cats and dogs). The most preferred recipients are humans.

5.5. Combination Therapy

The (R)-enantiomers of the subject compounds (or in certain embodiments, norfenfluramine racemate) may be usefully combined with one or more other therapeutic agent or as any combination thereof, in the treatment or prevention (as provided herein) of epilepsy or another epileptic seizure disorder in mammals, preferably humans. For example, the (R)-enantiomers of the subject compounds (or in certain embodiments, norfenfluramine racemate) may be administered simultaneously, sequentially or separately in combination with other therapeutic agents, including, but not limited to:

- TAAR1 agonists, such as phentermine (which according to non-limiting theory may increase norepinephrine release as a complement or supplement to, e.g., (R)- norfenfluramine effects on 5HT2C and/or 5HT2A receptors as described herein);

opiates analgesics, e.g., morphine, heroin, cocaine, oxymorphone, levorphanol, levallorphan, oxycodone, codeine, dihydrocodeine, propoxyphene, nalmefene, fentanyl, hydrocodone, hydromorphone, meripidine, methadone, nalorphine, naloxone, naltrexone, buprenorphine, butorphanol, nalbuphine and pentazocine;

non-opiate analgesics, e.g., acetaminophen, salicylates (e.g., aspirin);

nonsteroidal anti-inflammatory drugs (NSAIDs), e.g., ibuprofen, naproxen, fenoprofen, ketoprofen, celecoxib, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac;

anticonvulsants, e.g., carbamazepine, oxcarbazepine, lamotrigine, valproate, topiramate, gabapentin and pregabalin;

antidepressants such as tricyclic antidepressants, e.g., amitriptyline, clomipramine, despramine, imipramine and nortriptyline, COX-2 selective inhibitors, e.g., celecoxib, rofecoxib, parecoxib, valdecoxib, deracoxib, etoricoxib, and lumiracoxib;

alpha-adrenergics, e.g., doxazosin, tamsulosin, clonidine, guanfacine, dexmetatomidine, modafinil, and 4-amino-6,7-dimethoxy-2-(5-methane sulfonamido-1,2,3,4-tetrahydroisoquinol-2-yl)-5-(2-pyridyl) quinazoline;

barbiturate sedatives, e.g., amobarbital, aprobarbital, butabarbital, butabital, mephobarbital, metharbital, methohexital, pentobarbital, phenobartital, secobarbital, talbutal, theamylal and thiopental;

tachykinin (NK) antagonist, particularly an NK-3, NK-2 or NK-1 antagonist, e.g., (αR, 9R)-7-[3,5-bis(trifluoromethyl)benzyl)]-8,9,10,11-tetrahydro-9-methyl-5-(4-methylphenyl)-7H-[1,4]diazocino[2,1-g][1,7]-naphthyridine-6-13-dione (TAK-637), 5-[[2R,3S)-2-[(1R)-1-[3,5-bis(trifluoromethylphenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy5-(trifluoromethoxy)phenyl]-methylamino]-2-phenylpiperidine (2S,3S);

coal-tar analgesics, e.g., acetaminophen;

serotonin reuptake inhibitors, e.g., paroxetine, sertraline, norfluoxetine (fluoxetine desmethyl metabolite), metabolite demethylsertraline, '3 fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine, trazodone and fluoxetine;

noradrenaline (norepinephrine) reuptake inhibitors, e.g., maprotiline, lofepramine, mirtazepine, oxaprotiline, fezolamine, tomoxetine, mianserin, buproprion, buproprion metabolite hydroxybuproprion, nomifensine and viloxazine (Vivalan®)), especially a selective noradrenaline reuptake inhibitor such as reboxetine, in particular (S,S)-reboxetine, and venlafaxine duloxetine neuroleptics sedative/anxiolytics;

dual serotonin-noradrenaline reuptake inhibitors, such as venlafaxine, venlafaxine metabolite O-desmethylvenlafaxine, clomipramine, clomipramine metabolite desmethylclomipramine, duloxetine, milnacipran and imipramine;

acetylcholinesterase inhibitors such as donepezil;

5-HT3 antagonists such as ondansetron;

metabotropic glutamate receptor (mGluR) antagonists or agonists or allosteric potentiators of glutamate at mGluR's;

local anaesthetic such as mexiletine and lidocaine;

corticosteroid such as dexamethasone;

antiarrhythimics, e.g., mexiletine and phenytoin;

muscarinic antagonists, e.g., tolterodine, propiverine, tropsium t chloride, darifenacin, solifenacin, temiverine and ipratropium;

muscarinic agonists or allosteric potentiators of acetylcholine at muscarinic receptors cannabinoids or allosteric potentiators of endorphins at cannabinoid receptors;

vanilloid receptor agonists (e.g., resinferatoxin) or antagonists (e.g., capsazepine);

sedatives, e.g., glutethimide, meprobamate, methaqualone, and dichloralphenazone;

anxiolytics such as benzodiazepines, antidepressants such as mirtazapine, topical agents (e.g., lidocaine, capsaicin and resiniferotoxin);

muscle relaxants such as benzodiazepines, baclofen, carisoprodol, chlorzoxazone, cyclobenzaprine, methocarbamol and orphrenadine;

anti-histamines or H1 antagonists;

NMDA receptor antagonists;

5-HT receptor agonists/antagonists;

PDEV inhibitors;

Tramadol®;

cholinergic (nicotinic) analgesics;

alpha-2-delta ligands;

prostaglandin E2 subtype antagonists;

leukotriene B4 antagonists; and 5-lipoxygenase inhibitors.

As used herein "combination" refers to any mixture or permutation of an (R)-enantiomer of the subject compounds (or in certain embodiments, norfenfluramine racemate) with one or more additional therapeutic agents. Unless the context makes clear otherwise, "combination" may include simultaneous or sequentially delivery of the (R)-enantiomer of the subject compounds (or in certain embodiments, norfenfluramine racemate) with one or more therapeutic agents, including another (R)-enantiomer of the subject compounds. Unless the context makes clear otherwise, "combination" may include dosage forms of the (R)-enantiomer of the subject compounds (or in certain embodiments, norfenfluramine racemate) with another therapeutic agent. Unless the context makes clear otherwise, "combination" may include routes of administration of the (R)-enantiomer of the subject compounds (or in certain embodiments, norfenfluramine racemate) with another therapeutic agent. Unless the context makes clear otherwise, "combination" may include formulations of the (R)-enantiomer of the subject compounds (or in certain embodiments, norfenfluramine racemate) with another therapeutic agent. Dosage forms, routes of administration and pharmaceutical compositions include, but are not limited to, those described herein.

In one embodiment, the present disclosure relates to a method described herein comprising administering a therapeutically effective amount of an (R)-enantiomer of the subject compounds (or in certain embodiments, norfenfluramine racemate) simultaneously, sequentially or separately in combination with phentermine. Likewise, the present disclosure relates to a use described herein of an (R)-enantiomer of the subject compounds (or in certain embodiments, norfenfluramine racemate) simultaneously, sequentially or separately in combination with phentermine.

5.6. Kits-of-Parts

The present disclosure also provides kits that contain a pharmaceutical composition described herein. The kit also includes instructions for the use of the pharmaceutical composition for treating or preventing (as provided herein) epilepsy or another epileptic seizure disorder. Preferably, a kit will contain one or more unit doses of the pharmaceutical composition. For example, such a unit dose may be an amount sufficient for the preparation of an intravenous injection. It will be evident to those of ordinary skill in the art that such compositions which are light and/or air sensitive may require special packaging and/or formulation. For example, packaging may be used which is opaque to light, and/or sealed from contact with ambient air, and/or formulated with suitable coatings or excipients.

5.7. Preparation of the (R)-Enantiomers of the Invention

A. Preparation of (R)-Fenfluramine and (S)-Fenfluramine.

(R)-Fenfluramine and (S)-fenfluramine can be may be prepared using chiral synthons or chiral reagents by methods known to one skilled in the art, or resolved from fenfluramine using conventional techniques, such as HPLC using a chiral column. The optical resolution of fenfluramine by crystallization into its (R)-enantiomer and (S)-enantiomer was disclosed in, e.g., Coquerel et al., Chemistry Letters (1988), pp. 1081-1084.

B. Preparation of (R)-Norfenfluramine and (S)-Norfenfluramine.

(R)-Norfenfluramine and (S)-norfenfluramine can be may be prepared using chiral synthons or chiral reagents by methods known to one skilled in the art, or resolved from norfenfluramine (available commercially, e.g., from Toronto Research Chemicals, North York, Ontario, Canada) using conventional techniques, such as HPLC using a chiral column.

(R)-Norfenfluramine and (S)-norfenfluramine can also be prepared according to the methods disclosed in Reaction Schemes 1 and 2 below wherein the following abbreviations are used:

Raney Ni refers to Raney Nickel;
atm refers to atmosphere;
AcOH refers to acetic acid;
MeOH refers to methanol;
h refers to hours;
Pd/C refers to palladium on carbon; and
rt refers to room temperature.

Reaction Scheme 1 shows the preparation of (R)-norfenfluramine:

Reaction Scheme 1.

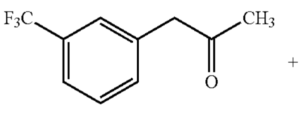

(101)

-continued

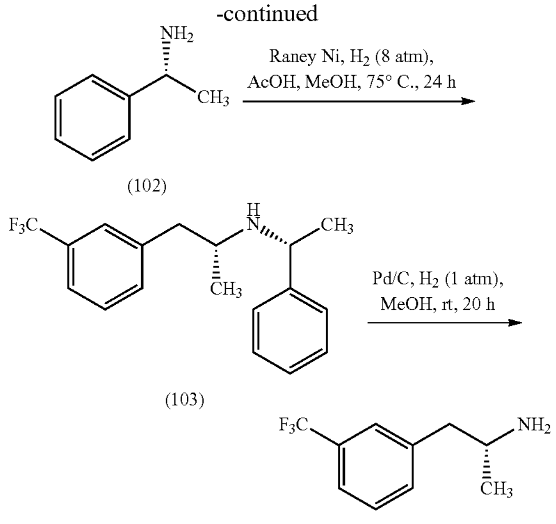

(102)

(103)

(R)-norfenfluramine

Compounds 101 and 102 are commercially available or can be prepared by methods known to one skilled in the art.

In general, (R)-norfenfluramine can be prepared by the method shown in Reaction Scheme 1 by first treating compound 101 with compound 102 under standard reductive amination conditions to form compound 103, which is then treated under standard catalytic hydrogenation conditions to form (R)-norfenfluramine.

In a similar manner, (S)-norfenfluramine is prepared as shown below in Reaction Scheme 2 wherein compounds 101 and 201 are commercially available:

Reaction Scheme 2.

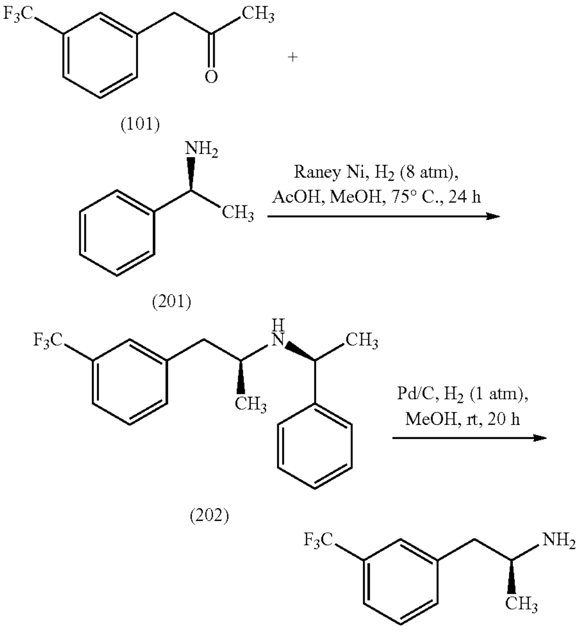

(101)

(201)

(202)

(S)-norfenfluramine

C. Preparation of (R)-Benfluorex and (S)-Benfluorex.

(R)-Benfluorex and (S)-benfluorex can be prepared from (R)-norfenfluramine and (S)-norfenfluramine by the methods disclosed in EP 1321445. Specifically, this methodology involves the reaction of (R)-norfenfluramine and (S)-norfenfluramine with ethylene oxide to form the corresponding amino alcohols, followed by acylation of the alcohol moiety with benzoyl chloride.

5.8. Numbered Embodiments

Embodiment 1. A method of treating a mammal having or at risk for having an epileptic seizure disorder, comprising administering to the mammal a therapeutically effective amount of one, two or all three of:

(i) (R)-fenfluramine or a pharmaceutically acceptable salt, solvate or prodrug thereof;

(ii) (R)-norfenfluramine or a pharmaceutically acceptable salt, solvate or prodrug thereof, and (iii) (R)-benfluorex or a pharmaceutically acceptable salt, solvate or prodrug thereof, wherein (R)-fenfluramine is substantially free of (S)-fenfluramine, (R)-norfenfluramine is substantially free of (S)-norfenfluramine and (R)-benfluorex is substantially free of (S)-benfluorex.

Embodiment 2. A method of treating a mammal having or at risk for having an epileptic seizure disorder, comprising administering to the mammal simultaneously or sequentially and in any order:

(a) a therapeutically effective amount of one, two or all three of:

(i) (R)-fenfluramine or a pharmaceutically acceptable salt, solvate or prodrug thereof, (ii) (R)-norfenfluramine or a pharmaceutically acceptable salt, solvate or prodrug thereof, and (iii) (R)-benfluorex or a pharmaceutically acceptable salt, solvate or prodrug thereof; and (b) a therapeutically effective amount of phentermine, or a pharmaceutically acceptable salt, solvate or prodrug thereof, wherein (R)-fenfluramine is substantially free of (S)-fenfluramine, (R)-norfenfluramine is substantially free of (S)-norfenfluramine and (R)-benfluorex is substantially free of (S)-benfluorex.

Embodiment 3. The method of either embodiment 1 or embodiment 2 wherein the epileptic seizure disorder is Dravet syndrome.

Embodiment 4. The method of either embodiment 1 or embodiment 2 wherein the epileptic seizure disorder is selected from photosensitive epilepsy, self-induced syncope, intractable epilepsy, Angelman syndrome, benign rolandic epilepsy, CDKL5 disorder, childhood and juvenile absence epilepsy, Dravet syndrome, frontal lobe epilepsy, Glut1 deficiency syndrome, hypothalamic hamartoma, infantile spasms/West's syndrome, juvenile myoclonic epilepsy, Landau-Kleffner syndrome, Lennox-Gastaut syndrome (LGS), epilepsy with myoclonic-absences, Ohtahara syndrome, Panayiotopoulos syndrome, PCDH19 epilepsy, progressive myoclonic epilepsies, Rasmussen's syndrome, ring chromosome 20 syndrome, reflex epilepsies, temporal lobe epilepsy, Lafora progressive myoclonus epilepsy, neurocutaneous syndromes, tuberous sclerosis complex, early infantile epileptic encephalopathy, early onset epileptic encephalopathy, generalized epilepsy with febrile seizures plus (GEFS+), Rett syndrome, multiple sclerosis, Alzheimer's disease, autism, ataxia, hypotonia, paroxysmal dyskinesia, focal onset seizures, generalized onset seizures, absence seizures, Jeavon Syndrome, epileptic encephalopathy, sunflower syndrome, fragile-X syndrome, alternating hemiplegia, autosomal dominant nocturnal frontal lobe epilepsy (ADNFLE), benign rolandic epilepsy, Doose Syndrome, early myoclonic encephalopathy, epilepsy of infancy with migrating focal seizures, epilepsy with generalized tonic-clonic seizures, epilepsy with myoclonic absences, epileptic encephalopathy with continuous spike and wave during sleep, juvenile absence seizures, progressive myoclonic epilepsies, SCN8A related epilepsy, SCN2A related epilepsy, KCNQ2 related epilepsy, and TBC1 Domain Containing Kinase (TBCK) related intellectual disability (ID) syndrome.

Embodiment 5. A method of treating a mammal having or at risk for having an epileptic seizure disorder, comprising administering to the mammal a therapeutically effective amount of racemic norfenfluramine [(R,S)-1-(3-(trifluoromethyl)phenyl)propan-2-amine].

Embodiment 6. A method of treating a mammal having or at risk for having an epileptic seizure disorder, comprising administering to the mammal simultaneously or sequentially and in any order:

(a) a therapeutically effective amount of racemic norfenfluramine [(R,S)-1-(3-(trifluoromethyl)phenyl)propan-2-amine]; and (b) a therapeutically effective amount of phentermine, or a pharmaceutically acceptable salt, solvate or prodrug thereof.

Embodiment 7. The method of either embodiment 5 or embodiment 6 wherein the epileptic seizure disorder is Dravet syndrome.

Embodiment 8. The method of either embodiment 5 or embodiment 6 wherein the epileptic seizure disorder is selected from photosensitive epilepsy, self-induced syncope, intractable epilepsy, Angelman syndrome, benign rolandic epilepsy, CDKL5 disorder, childhood and juvenile absence epilepsy, Dravet syndrome, frontal lobe epilepsy, Glut1 deficiency syndrome, hypothalamic hamartoma, infantile spasms/West's syndrome, juvenile myoclonic epilepsy, Landau-Kleffner syndrome, Lennox-Gastaut syndrome (LGS), epilepsy with myoclonic-absences, Ohtahara syndrome, Panayiotopoulos syndrome, PCDH19 epilepsy, progressive myoclonic epilepsies, Rasmussen's syndrome, ring chromosome 20 syndrome, reflex epilepsies, temporal lobe epilepsy, Lafora progressive myoclonus epilepsy, neurocutaneous syndromes, tuberous sclerosis complex, early infantile epileptic encephalopathy, early onset epileptic encephalopathy, generalized epilepsy with febrile seizures plus (GEFS+), Rett syndrome, multiple sclerosis, Alzheimer's disease, autism, ataxia, hypotonia, paroxysmal dyskinesia, focal onset seizures, generalized onset seizures, absence seizures, Jeavon Syndrome, epileptic encephalopathy, sunflower syndrome, fragile-X syndrome, alternating hemiplegia, autosomal dominant nocturnal frontal lobe epilepsy (ADNFLE), benign rolandic epilepsy, Doose Syndrome, early myoclonic encephalopathy, epilepsy of infancy with migrating focal seizures, epilepsy with generalized tonic-clonic seizures, epilepsy with myoclonic absences, epileptic encephalopathy with continuous spike and wave during sleep, juvenile absence seizures, progressive myoclonic epilepsies, SCN8A related epilepsy, SCN2A related epilepsy, KCNQ2 related epilepsy, and TBC1 Domain Containing Kinase (TBCK) related intellectual disability (ID) syndrome.

The following Examples, which are directed to the synthesis of the enantiomers of the subject compounds; and the following Biological Examples are provided as a guide to assist in the practice of the present methods and use of the subject compounds, and are not intended as a limitation on the scope of the claimed invention.

6. EXAMPLES

6.1. Synthetic Example 1

Synthesis of (R)-norfenfluramine ((R)-1-((3-trifluoromethyl)phenyl)propan-2-amine)

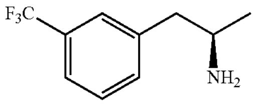

A. To a mixture of 1-(3-(trifluoromethyl)phenyl)propan-2-one (10.0 g, 49.5 mmol) in methanol (60 mL) was added (R)-1-phenylethan-1-amine (6.00 g, 49.5 mmol), Raney nickel (800 mg of a 50% w/w slurry in water) and glacial acetic acid (1.49 g). The mixture was purged for 5 minutes with hydrogen gas, heated to 75° C. and stirred for 24 h under a hydrogen atmosphere (8 atm). The mixture was allowed to cool to ambient temperature and was filtered through pad of diatomaceous earth. The pH of the filtrate was adjusted to pH~1 by the addition of concentrated hydrochloric acid (5 mL). Water (30 mL) was added and the mixture was stirred at 40° C. for 1 h. The mixture was then cooled to 5° C. and allowed to stand for 20 minutes at this temperature, during which time a colorless precipitate was deposited. The solid was collected by filtration and washed with a mixture of methanol and water (1:1 v/v, 200 mL) to afford (R)—N—((R)-1-phenylethyl)-1-(3-(trifluoromethyl)phenyl)propan-2-amine (7.65 g, 22.2 mmol, 45%) as its corresponding hydrochloride salt. The filtrate was concentrated to dryness in vacuo and the residue washed with diethyl ether (3×30 mL) to afford a further quantity of (R)—N—((R)-1-phenylethyl)-1-(3-(trifluoromethyl)phenyl)propan-2-amine (4.52 g, 13.1 mmol, 26%) as its corresponding hydrochloride salt. The total yield was 71%.

B. A solution of (R)—N—((R)-1-phenylethyl)-1-(3-(trifluoromethyl)phenyl)propan-2-amine hydrochloride (2.23 g, 6.50 mmol) in methanol (25 mL) was purged with dry nitrogen for 10 minutes. Palladium on carbon (0.44 g, 10% w/w Pd) was added. The mixture was purged with dry nitrogen for 10 minutes and subsequently with hydrogen for 10 minutes. The mixture was then stirred for 20 h under a hydrogen atmosphere (1 atm, balloon) and filtered through a pad of diatomaceous earth. The filtrate was concentrated to dryness in vacuo and the residue was dissolved in 0.2 M hydrochloric acid (20 mL). The resultant solution was washed with hexanes (3×20 mL) and the pH of the aqueous layer was then adjusted to pH~12 by the addition of sodium hydroxide (~1 g). The mixture was extracted with ethyl acetate (3×20 mL) and the combined organic extracts washed with saturated aqueous sodium chloride (50 mL), dried over anhydrous sodium sulfate and concentrated to dryness in vacuo to afford (R)-norfenfluramine ((R)-1-((3-trifluoromethyl)phenyl)propan-2-amine) (1.12 g, 5.52 mmol, 85%) as a colorless oil. 1H NMR (400 MHz, $CDCl_3$): δ 7.52-7.39 (m, 4H), 3.22-3.18 (m, 1H), 2.80-2.73 (m, 1H), 2.63-2.56 (m, 1H), 1.13 (d, J=6.0 Hz, 3H); MS (ES+) 204.2 (M+H); [α]D20−16.0° (c=1.0, CHCl3).

6.2. Synthetic Example 2

Synthesis of (S)-norfenfluramine ((S)-1-((3-trifluoromethyl)phenyl)propan-2-amine)

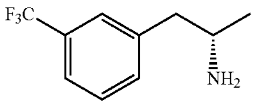

A. To a mixture of 1-(3-(trifluoromethyl)phenyl)propan-2-one (10.0 g, 49.5 mmol) in methanol (60 mL) was added (S)-1-phenylethan-1-amine (6.00 g, 49.5 mmol), Raney nickel (800 mg of a 50% w/w slurry in water) and glacial acetic acid (1.49 g). The mixture was purged for 5 minutes with hydrogen gas, heated to 75° C. and stirred for 24 h under a hydrogen atmosphere (8 atm). The mixture was allowed to cool to ambient temperature and was filtered through pad of diatomaceous earth. The pH of the filtrate was adjusted to pH~1 by the addition of concentrated hydrochloric acid (5 mL). Water (30 mL) was added and the mixture was stirred at 40° C. for 1 h. The mixture was then cooled to 5° C. and allowed to stand for 20 minutes at this temperature, during which time a colorless precipitate was deposited. The solid was collected by filtration and washed with a mixture of methanol and water (1:1 v/v, 200 mL) to afford (S)—N—((S)-1-phenylethyl)-1-(3-(trifluoromethyl)phenyl)propan-2-amine (8.01 g, 23.3 mmol, 47%) as its corresponding hydrochloride salt. The filtrate was concentrated to dryness in vacuo and the residue washed with diethyl ether (3×30 mL) to afford a further quantity of (S)—N—((S)-1-phenylethyl)-1-(3-(trifluoromethyl)phenyl)propan-2-amine (4.78 g, 13.9 mmol, 28%) as its corresponding hydrochloride salt. The total yield was 75%.

B. A solution of(S)—N—((S)-1-phenylethyl)-1-(3-(trifluoromethyl)phenyl)propan-2-amine hydrochloride (2.23 g, 6.50 mmol) in methanol (25 mL) was purged with dry nitrogen for 10 minutes. Palladium on carbon (0.44 g, 10% w/w Pd) was added. The mixture was purged with dry nitrogen for 10 minutes and subsequently with hydrogen for 10 minutes. The mixture was then stirred for 20 h under a hydrogen atmosphere (1 atm, balloon) and filtered through a pad of diatomaceous earth. The filtrate was concentrated to dryness in vacuo and the residue was dissolved in 0.2 M hydrochloric acid (20 mL). The resultant solution was washed with hexanes (3×20 mL) and the pH of the aqueous layer was then adjusted to pH~12 by the addition of sodium hydroxide (~1 g). The mixture was extracted with ethyl acetate (3×20 mL) and the combined organic extracts washed with saturated aqueous sodium chloride (50 mL), dried over anhydrous sodium sulfate and concentrated to dryness in vacuo to afford (S)-norfenfluramine ((S)-1-((3-trifluoromethyl)phenyl)propan-2-amine) (1.16 g, 5.72 mmol, 88%) as a colorless oil. 1H NMR (400 MHz, $CDCl_3$): δ 7.52-7.39 (m, 4H), 3.22-3.18 (m, 1H), 2.80-2.73 (m, 1H), 2.63-2.56 (m, 1H), 1.13 (d, J=6.0 Hz, 3H); MS (ES+) 204.2 (M+H); [α]D20+16.0° (c=1.0, CHCl3).

6.3. Biological Assays

Various techniques are known in the art for testing the activity of the (R)-enantiomers of the invention. In order that the invention described herein may be more fully understood, the following biological assays are set forth. It should be understood that these examples are for illustrative purposes only and are not to be construed as limiting this invention in any manner.

6.3.1. Biological Example 1. Dravet Syndrome Mouse Model

Dravet Syndrome, an epileptic encephalopathy is caused by a heterozygous loss-of-function (LOF) mutation in the gene encoding the neuron-specific voltage-gated sodium channel, SCN1A. Mice having a heterozygous targeted deletion of the gene encoding SCN1A recapitulate many features of Dravet syndrome and provide a useful disease model in which to test fenfluramine and fenfluramine-related compounds as described herein, including isolated enantiomers of such compounds. Heterozygous Scn1a knockout (Scn1a+/−) mice also have seizures and are a model of Dravet Syndrome.

For example, Scn1a+/−F1 mice on strains 129S6/SvEvTac and C57BL/6J exhibit severe epilepsy and premature lethality and are considered to be a mammalian model of Dravet syndrome in humans. Reduced sodium current (INa) density as well as impaired action potential firing were described in hippocampal interneurons of F1 Scn1a+/− mice, resulting in reduced action potential-dependent inhibitory GABAergic neurotransmission and enhanced neuronal excitability (Han et al., 2012 *Nature* 489:385; Mistry et al., 2014 *Neurobiol. Dis.* 65:1). These mice are susceptible to hyperthermia-induced seizures from the third week of life, as reported by Oakley et al., (2009) *Proc. Natl. Acad. Sci. U.S.A.* 106(10):3994-3999; Oakley et al., (2013)*J. Pharmacol. Exrp. Ther.* 345(2):215-224).

Flurothyl seizure induction. Scn1a+/−F1 mice between 5 and 12 weeks of age are placed in a clear Plexiglas™ (Poly(methyl methacrylate), PMMA), chamber, and flurothyl (2,2,2-trifluroethylether) (Sigma-Aldrich, St. Louis, MO) is slowly introduced into the chamber via a syringe pump at a rate of 20 ml/min and allowed to volatilize. Seizure thresholds are determined by measuring the latency to the first MJ (myoclonic jerk) and to the GTCS (generalized tonic clonic seizure). The seizure thresholds can be measured when the mice are dosed with vehicle control or active compound (e.g., isolated fenfluramine enantiomer) administered in vehicle. The MJ is the first observable behavioral response, and is characterized by a brief jerk of the shoulders and/or neck. The GTCS is characterized by convulsions of the entire body and a loss of posture. The mice are also scored for progression of the GTCS to tonic hind-limb extension.

KA seizure induction. Scn1a+/−F1 mice between 3 and 4 months of age are injected intraperitoneally (i.p.) with 15, 20 or 30 mg/kg kainic acid KA (Ocean Produce International, Shelburne, Nova Scotia, Canada). KA is dissolved in 0.9% (wt/vol) aqueous saline to a concentration of 2.5 mg/ml in order to obtain an appropriate injection volume. All mice are injected between 12 noon and 4 p.m. to minimize behavioral variation due to circadian rhythm. After the injection of KA, mice are observed for 2 h and scored according to a modified Racine scale (Racine, R. J. 1972 *Electroencephalogr. Clin. Neurophysiol.* 32(3):281-294). This modified scale is based on the following criteria: stage 0—no response; stage 1—staring; stage 2—head nodding; stage 3—forelimb clonus; stage 4—rearing and falling; stage 5—GTCS; stage 6—death. The modified Racine scale scores are compared for mice dosed with vehicle alone (control) and mice receiving active fenfluramine-derived compound.

Temperature-induced seizures assay. Seizures are achieved by inducing hyperthermia in Scn1a+/−F1 mouse pups. A P14 to P22 mouse is placed in a Plexiglas™ PMMA chamber, the bottom of which is lined with absorbent paper. Mouse body core temperature is monitored by a rectal temperature probe connected to a rodent temperature controller and mice are allowed to acclimate to the PMMA test chamber for 10 minutes, maintaining their core temperature at 37.0° C. Core temperature is then raised by 0.5° C. every 2 min through the use of a heat lamp positioned above the test chamber until behaviors indicating seizures begin, or until the body core temperature reaches 42.5° C. Core temperature at the onset of the seizures, behavior and time are noted. The maximal duration of hyperthermia is 22 minutes.

Experimental and Clinical Endpoints: A seizure is defined as myoclonic jerks, clonus of the forepaw, and/or tonic extension of the limbs. Latency and duration of seizure are recorded. Compounds with pro-convulsant activity decrease the latency to seizure while compounds with anti-convulsant activity increase it. The overall duration of hyperthermia exposure is 22 minutes and all animals are euthanized at the end of assay.

Thermal Induction and EEG. In a group of Scn1a+/−F1 mice, each animal's core body temperature is continuously monitored by a rectal temperature probe and controlled by a feedback circuit in line with a heat lamp. Body temperature is increased in 0.5° C. steps at 2-min intervals until a seizure occurs or a temperature of 42° C. is reached. The seizure threshold is measured by the latency to first seizure and is compared when mice are dosed with vehicle (control) or active compound administered in the vehicle. The animal is then cooled and returned to its home cage. Thermal induction is performed on P22, and the induction process and resulting seizures are recorded by video monitoring. Seizures are scored on the Racine scale using the same criteria as described below under spontaneous seizure recording and analysis.

Spontaneous Seizure Recording and Analysis. Scn1a+/−F1 mice are continuously video monitored from P19 to P27. The resulting video files are reviewed, for example, at ~8× speed. Suspected seizure events are then reviewed at a decreased speed, for example at 2× speed, and scored from 1 to 5 for seizure severity on the basis of the Racine scoring system: 1, mouth and facial movements; 2, head nodding; 3, forelimb clonus, usually one limb; 4, forelimb clonus with rearing; and 5, generalized tonic-clonic seizure (GTC), rearing, clonus, and falling over. The Racine scores are compared for mice dosed with vehicle alone (control) versus those dosed with active compound in the vehicle (test).

On the C57BL/6J (B6) background, 50% of Scn1a+/− null heterozygotes develop spontaneous seizures and sporadic death beginning in the third week of life (Yu et al., 2006 *Nat. Neurosci.* 9:1142-1149; Mistry et al., 2014 *Neurobiol. Dis.* 65:1-11). P17-P20 heterozygous mice (n=2-4) are placed in a recording chamber. Food and water are provided ad libitum. Mouse behavior is recorded continuously 24 hours a day for 10 to 14 days using analog cameras (one per chamber) connected to a DVR recorder or a computer. Mice are sacrificed within five hours after the last recording. A control group of mice treated with vehicle alone is included in any studies testing the efficacy of candidate AEDs against spontaneous seizures. Compounds are administered daily or chronically using an osmotic pump according to the manufacturer's instructions (Alzet Inc., Cupertino, CA, USA) depending on their properties.

Analysis of Video Files: Investigators unaware of the experimental group status (control vs. test compound) analyze the videos, scanning for behavioral seizures either manually or using seizure detection software (Ethovision XT, Noldus Information Technology, Leesburg, VA).

Statistical analysis. For parametric data sets, statistical analysis is performed using the Student t-test. Dichotomous data sets (the number of mice exhibiting a GTCS and the mortality rates) are analyzed for statistical significance using the Fisher Exact test, while non-parametric data (the KA seizure stage) are analyzed using a Mann-Whitney Rank Sum test.

The following examples describe other in vivo epilepsy models in which to test the (R)-enantiomers of the present disclosure.

6.3.2. Biological Example 2. 6 Hz Seizure Test

This assay tests the ability of a test compound to block a psychomotor seizure induced by long-duration, low frequency (6 Hz) stimulation, and provides an art-accepted model of therapy-resistant partial seizure (Brown et al., 1953 *J. Pharmacol. Exp. Therapeut.* 107(3):273-283; White H S, Woodhead J H, Wilcox K S, General principles: discovery and preclinical development of antiepileptic drugs, In: Levy R H, Mattson R H, Meldrum B S, Perucca E, editors. Antiepileptic drugs 5th ed Philadelphia: Lippincott Williams & Wilkins; 2002. pp. 36-48; Hartman et al., 2008 *Epilepsia* 49(2):334-339).

Investigational compounds such as the herein described (R)-enantiomers of the invention (e.g., "test compounds"), including those found to be inactive in either the maximal electroshock seizure (MES) (Suzuki et al., 1995 *Neuroscience* 64(3):665-674; Bouilleret et al., 1999 *Neuroscience* 89(3):717-729; Riban et al., 2002 *Neuroscience* 112(1): 101-111) or subcutaneous Metrazol (s.c. Met) (Swinyard, E. A., 1969 *Epilepsia* 10(2): 107-119) tests, are screened for their ability to block psychomotor seizures induced by a low-frequency (6 Hz), long-duration (3 sec) stimulus delivered through corneal electrodes. For example, levetiracetam is highly effective (ED50: 19 mg/kg, 30 min after i.p. injection) in the 6 Hz model originally described in the early 1950's (Toman et al., 1952 Texas Reports on Biology and Medicine 10:96; Swinyward, E. A. Electrically induced convulsions, in Experimental Models of Epilepsy, D. B. Purpura, et al., Editors. 1972, Raven Press: New York. pp. 443-458; Swinyard, E. A., Experimental Models of Epilepsy: A Manual for the Laboratory Worker, in Electrically Induced Convulsions, eds. J. K. P. D. P Purpura, D. Tower, D. M. Woodbry, R. Walter. 1972, New York: Raven Press, pp. 433-438) whereas it is ineffective in the MES test (Barton et al., 2001 *Epilepsy Res.* 47(3):217-227). Furthermore, the 6 Hz test demonstrates partial to complete resistance to known Na+ channel blockers including many AEDs, thus making this test useful as an early identification and differentiation screen for candidate AEDs. Compounds found to be effective in this low-frequency (6 Hz), long-duration assay may therefore be effective in the treatment of therapy-resistant partial seizures.

Methods. Adult male CF1 mice (18-25 g) are pretreated intraperitoneally (i.p.) with the test compound at a dose of 20-100 mg/kg. If toxicity is noted in a pre-test screen for toxic effects when the test compound is administered i.p. at varying dosages, the dose is modified to avoid overt toxic effects. Each treatment group (n=4-16 mice/group) is examined for anticonvulsive effects at one or more of five time points (¼, ½, 1, 2, and 4 hr) after treatment with the test compound. Following pretreatment, each mouse receives a drop of 0.5% tetracaine hydrochloride applied to each eye. The mouse is then challenged with low-frequency (6 Hz) stimulation for 3 sec delivered through corneal electrodes. The low-frequency, long-duration stimuli are initially delivered at 32 mA intensity. Animals are manually restrained and released immediately following the stimulation and observed for the presence or absence of seizure activity. If the test compound is effective in the 32 mA screen, an additional assay is performed in which the stimulation current is increased to 44 mA but otherwise using the same protocol as described above. For dose-response studies, an n of 8 mice is used per dose and a dose-response curve is generated at the time of peak effect (TPE) at the specific stimulation intensity.

Typically, the 6 Hz stimulation results in a seizure characterized by a minimal clonic phase that is followed by stereotyped, automatistic behaviors, including jaw clonus, forelimb clonus, twitching of the vibrissae, and/or Straub-tail. Animals not displaying such behaviors are considered protected. Seizure score can be used as an additional measure of the efficacy of the investigational compound (Racine, R. J. 1972 *Electroencephalogr. Clin. Neurophysiol.* 32(3): 281-294). Data are analyzed by Mann-Whitney U test, with $p<0.05$ determined to be statistically significant. For data obtained at each time point, results are expressed as the total number of animals protected out of the number of animals tested over time (e.g., 2/4 represents 2 out of 4 mice tested are protected).

Test compounds that produce anticonvulsant effects (e.g., at least 2/4 protected at two or more time points) are optionally tested in other models of chronic epilepsy or pharmacoresistance, including the corneal kindled mouse test (Rowley and White 2010 *Epilepsy Res.* 92(2-3): 163-169), the hippocampal kindled rat test (Lothman, E. W. 1988 *Epilepsy Res.* 2(6):367-379) or the lamotrigine-resistant amygdala kindled rat test (Srivastava and White 2013 *Epilepsy Res.* 104:26).

Typical seizures induced by the 6 Hz model display an initial momentary stun followed immediately by forelimb clonus, twitching of the vibrissae, and Straub tail (Barton et al., 2001). These behaviors provide translation relevance as they were originally described as being similar to the aura of human patients with partial seizures (Toman et al., 1952 *Texas Reports on Biology and Medicine* 10:96; Roman, J. E. P., 1951 *Neurology* 1:444). 6 Hz seizures are sensitive to the benzodiazepines, succinamides, barbiturates, valproic acid and other AEDs that elevate seizure threshold (Barton et al., 2001).

6.3.3. Biological Example 3. Hippocampal Kindled Rat Model

This model tests the ability of a test compound to block behavioral seizures and/or decrease the afterdischarge duration (ADD) in a hippocampal kindled rat model of focal seizures. The kindling model has been a useful adjunct to the more traditional anticonvulsant tests to identify a test substance's potential utility for treating complex partial seizures. The hippocampal kindled rat provides an experimental model of focal seizures that become secondarily generalized, for example, the hippocampal kindling model described by Lothman and colleagues (Lothman, E. W. 1988).

Methods. Animals are first surgically prepared for kindling acquisition. Adult, male Sprague-Dawley rats (275-300 g) are surgically implanted with bipolar electrodes (Lothman, E. W. 1988). Briefly, a bipolar electrode is stereotaxically implanted into the ventral hippocampus (AP −3.6, ML −4.9, VD −5.0 from dura, incisor bar +5.0) under ketamine-xylazine anesthesia. Animals are allowed to recover for one week before the kindling regimen begins. The rapid hippocampal kindling paradigm consists of applying a repeated stimulation regimen on alternating days for a total of 5 stimulus days, as described previously (Lothman and Williamson 1994 *Brain Res.* 649(1-2):71-84). During the stimulation regimen, a 50 Hz, 10 sec train of 1 ms biphasic 200 μA pulses is delivered every 30 min for 6 hours, thereby giving 12 stimulations per stimulus day. Once animals are kindled to consistently present with a Stage 5 behavioral seizure, the test compound is evaluated for its ability to modify the fully expressed kindled seizure and afterdischarge duration after a one-week, stimulation-free period. Each kindled rat is allowed at least five days between tests to "washout" any investigational compound after testing.

Focal Seizures in Hippocampal Kindled Rats. Candidate substances are evaluated for their ability to block fully kindled secondarily generalized seizures after kindling acquisition (Lothman, E. W. 1988). The behavioral seizure scores (BSS) are rated according to the following criteria (Racine, R. J. 1972):

Stage 1—mouth and facial clonus
Stage 2—stage 1 plus head nodding
Stage 3—stage 2 plus forelimb clonus
Stage 4—stage 3 plus rearing
Stage 5—stage 4 plus repeated rearing and falling For the following tests ("Test 11", "Test 12", Test 13"), the mean values and S.E.M. are calculated for the afterdischarge duration (ADD), and p values are determined by Student's t-test. Significant differences in BSS from control and treated groups are determined by the non-parametric Mann-Whitney U test, with $p<0.05$ determined to be statistically significant.

Test 11: Identification of Neurotoxicity and Ability to Block Hippocampal-Kindled Focal Seizures.

In preparation for the hippocampal kindled rat test, an appropriate dose of the candidate AED (devoid of minimal motor impairment (MMI)) is determined. For the MMI study, three groups of two rats per time point are administered the test compound at 300, 100, and 30 mg/kg and MMI is monitored at ¼, ½, 1, 2, and 4 hr in an open field. Based on the results from the MMI study, two kindled rats are then administered a non-toxic dose of the test drug and given the kindled stimulation at 15, 45, 75, 105, 135, 165, and 195 min post-drug administration. The effects of the treatment on their BSS and afterdischarge duration are recorded. If the results from this initial screen suggest that a candidate AED possesses activity against the fully expressed kindled seizure, the group size is increased to eight rats for subsequent testing (Tests 12 and 13).

For each time group, results are expressed as the total number of animals protected out of the number of animals tested over time (e.g., 2 out of 2 protected). Test compounds that produce anticonvulsant effects (e.g., at least ½ protected at two or more time points) will then be rescreened with an increased n (e.g., n=6-8). Active compounds are then candidates for other models of pharmacoresistance, including the 6 Hz test (supra) and the lamotrigine-resistant amygdala kindled rat test (Srivastava and White 2013 *Epilepsy Res.* 104:26)

Test 13: Quantitation of a Candidate Anti-Epilepsy Drug's Ability to Block Focal Seizures Based on BSS.

Separate groups of kindled rats (n=6-8) receive escalating doses of the candidate AED based on the results from Test 11 (supra). Rats are then tested at 15, 45, 75, 105, 135, 165, and 195 min after drug administration. The BSS and ADD of each rat are noted, with mean and S.E.M. being calculated. Animals displaying a seizure score of 3 or less are considered protected. These data are used to establish a dose-response curve and subsequent ED50. Significant changes in ADD are also recorded. When a candidate AED (test drug) is observed to significantly lower both the seizure score (3 or lower) and the afterdischarge duration (ADD), a dose-response study is initiated. The BSS and ADD for each dose are averaged at the time of peak effect (TPE), and the mean and the S.E.M. are compared to control values by the non-parametric Mann-Whitney U test. The ability of a candidate AED to reduce seizure severity is quantitated and an ED50 is determined by probit analysis.

The BSS and ADD for each dose of the candidate AED are averaged at the TPE, the S.E.M. calculated, and compared to control values. The ability of a candidate substance to reduce seizure severity is quantified by results collected from several doses demonstrating protection ($BSS \leq 3$) and an ED50 is determined by probit analysis.

Test 12: Effect on Afterdischarge Threshold in Hippocampal Kindled Rats.

This animal model assay evaluates the ability of a candidate anti-epilepsy drug (AED) to increase the Afterdischarge Threshold (ADT) in the fully kindled rat. The initial stimulation is conducted at an intensity of 20 μA. Stimulus intensity is increased in 10 μA increments every 1-2 min until an afterdischarge is elicited. Fifteen minutes after the pre-drug threshold determination, a single dose of the test drug is administered to each of two animals. The ADT is then re-determined for each individual rat at varying times, e.g., ¼, 1, 2, and 4 hours after drug administration. Both BSS and ADD are recorded at each of the time points tested. The seizure score and ADD are also recorded at the ADT. Behavioral seizures are scored according to the criteria described above (Racine, R. J. 1972). Individual seizure scores, ADDs, and ADTs are recorded. In the case of a candidate (test) drug exhibiting putative AED activity, four or more animals are used, and the results are then averaged and the group mean and S.E.M. are calculated.

6.3.4. Biological Example 4. Chemoconvulsant Model

This model assesses the effect of a candidate AED against the effects of the known chemoconvulsants, bicuculline and picrotoxin. In this art-accepted animal model, a seizure is induced by the GABA A receptor (GABAA) antagonist, bicuculline (BIC), and the GABAA chloride-channel blocker, picrotoxin (PIC) (see, e.g., White et al., 2012 *Epilepsia* 53(1): 134-146; Shih et al., 2001 *Toxicol.* 162(1): 35-42; White et al., 1997 *Epilepsy Res.* 28:167; Swinyard et al., 1993 *Epilepsy Res.* 15(1):35-45; Coleman et al., 1985 *Life Sci.* 37(8):749-755; Wood, J. D. 1975 *Prog. Neurobiol.* 5:77-95; Snodgrass, S. R. 1992 *J. Child Neurol.* 7(1):77-86; Newland and Cull-Candy 1992 *J. Physiol.* 447(1):191-213).

Methods. In initial studies, the test drug (candidate AED) is administered to laboratory mice at various dosages in a suitable vehicle to assess its ability to prevent a clonic seizure produced by the subcutaneous (s.c.) injection of either BIC (2.7 mg/kg) or PIC (2.5 mg/kg); control groups receive vehicle and either BIC or PIC, or vehicle only. Following the administration of BIC, CF1 mice are placed in isolation cages and observed for 30 min for the presence or absence of a seizure; those receiving PIC are observed for 45 min because of the slower absorption of this convulsant. BIC- and PIC-induced seizures typically consist of an episode of clonic spasms of the fore- and hind limbs, jaws and vibrissae. BIC-induced clonic seizures are generally followed by tonic extension of the hind limbs and death.

For candidate AED compounds at dosages that exhibit an ability to prevent, delay the onset of, or reduce the severity of clonic seizure in the initial studies, activity is quantified in follow-up groups of eight animals and the ED50 and 95% confidence interval of the test compound is determined by probit analysis.

6.3.5. Biological Example 5. Zebrafish Model

This model assesses the effect of a candidate AED in vivo in an art-accepted model employing mutant zebrafish (*Danio rerio*) for behavioral and electrophysiologic characterization of AED effects in an intact vertebrate organism (Dinday et al., 2015 ENEURO 2(4) e0068-15.2015 1-19). Zebrafish that are homozygous for a mutation in the neuronal voltage-gated sodium channel scn1Lab recapitulate a Dravet syndrome-like phenotype characterized by seizures, early fatality, and resistance to several AEDs. Homozygous mutant scn1Lab zebrafish are bred and selected as described (Dinday et al., 2015).

Seizure Monitoring. For assessment of candidate AED effects on zebrafish behavior, single homozygous mutant scn1Lab larvae (5-6 days post-fertilization) are placed in individual wells of a flat-bottomed 96-well plate in "embryo medium" (Dinday et al., 2015) containing methylene blue, in the absence or presence of 1-500 μM (e.g., 100 μM) candidate AED, and monitored for swimming activity using motion-detecting video equipment with locomotion-plotting software as described (Id.). Activity is rated on a scale of zero (little or no swim activity), stage I (brief episodes of swim activity), stage II (rapid swimming in circles), or stage III (paroxysmal whole body convulsions with brief loss of posture). Candidate AEDs that reduce activity levels from stage II or stage III to stage zero or stage I without toxicity are considered to have potential anti-seizure activity for electrophysiology follow-up.

Electrophysiology. Electrophysiologic measurements are made of the same organisms in which apparent AED anti-seizure activity without toxicity is observed in at least two independent trials of the swim activity test, as described (Dinday et al., 2015). Briefly, the zebrafish are transiently paralyzed with α-bungarotoxin (1 mg/ml) and immobilized in 1.2% agarose, and desired specific forebrain structures (e.g., telencephalon, optic tectum, etc.) are contacted with local field electrodes for electroencephalography to assess epileptiform electrographic discharge activity in the absence or presence of the candidate AED as described (Id.).

6.3.6. Biological Example 6. Anticonvulsant Effects in the 6 Hz Seizure Test In Vivo In this Example, the in vivo anticonvulsant effects of candidate AEDs were tested in mice using the 6 Hz seizure test. The 6 Hz seizure test was performed essentially as described above in Biological Example 2, with minor modifications as presented here, including data collection at a time point that was one hour after administration of the candidate AEDs.

Materials and Methods

Compounds: Candidate AED compounds were prepared as described above unless otherwise noted, and were as follows:

Racemic fenfluramine ([rac]-fenfluramine hydrochloride);

(R)-fenfluramine ([R]-(−)-fenfluramine hydrochloride);

Racemic norfenfluramine ([rac]-norfenfluramine) was purchased from Toronto Research Chemicals, North York, Ontario, Canada;

(R)-norfenfluramine ([R]-(−)-norfenfluramine.

Animals: Adult male CF-1 albino mice (25-35 g) purchased from Harlan-Envigo (East Millstone, NJ). The mice were housed four per cage and had access to filtered water and chow ad libitum, throughout the experiment.

Compound Preparation and Administration: All four compounds were solubilized in sterile aqueous saline solution (0.9% NaCl). Compounds were administered to animals (16 mice in each treatment group) via intraperitoneal (IP) injection at 10 ml/kg volume, one hour prior to the assay. Control animals received vehicle (saline) only.

6 Hz Assay: Candidate AED compounds were screened for their ability, one hour after administration to test animals, to block psychomotor seizures induced by a low-frequency (6 Hz) alternating current (44 mA), long-duration (3 sec) stimulus that was delivered through corneal electrodes. These seizures are believed to model partial seizures observed in humans. A drop of 0.5% Alcaine solution was placed on the cornea of each animal's eye prior to delivery of electric current delivery. Electrodes connected to a regulated power supply (Model 57800 Electro-Convulsive Therapy Unit, Ugo Basile Srl, Gemonio, Italy) were subsequently placed gently onto the eyes of the animal and the electrical shock was initiated by triggering a three-second current pulse (6 Hz, 44 mA) using a foot-pedal actuator. The animals were restrained by hand and gently released as the electric shock was delivered and the seizure commenced. Typically, the seizure was characterized by an initial momentary stun followed immediately by jaw clonus, forelimb clonus, twitching of the vibrissae, and Straub tail lasting for at least one second. Animals not displaying this behavior were considered "protected".

Pharmacological distribution and bioanalysis. Immediately following characterization of seizure behaviors in the 6 Hz assay, animals were humanely sacrificed and brain and plasma samples were collected for analysis of the distribution of the administered compounds to these tissue compartments.

Brain sample homogenization. Pre-weighed whole mouse brains were thawed and 1 mL of deionized water and 1 mL of acetonitrile were added to each sample vial containing brain tissue. The samples were homogenized using a handheld Omni™ TH homogenizer (Omni International, Kennesaw, GA, USA) until a uniform slurry was obtained. 1 mL aliquots of the slurry were transferred to clean 1.5 mL plastic Eppendorf tubes and the tubes were centrifuged at 13,000 rpm (15,871×g) for 20 minutes. The supernatant was collected and stored in clean labelled plastic Eppendorf vials at −80° C.

Mouse plasma and brain homogenate sample preparation. Mouse brain homogenates and mouse plasma samples, as well as calibration standards and QC samples prepared from control ("blank") untreated mouse plasma, were extracted by protein precipitation. Briefly, 50 μL of each brain homogenate and mouse plasma sample (as well as each calibration standard, QC sample and blank mouse plasma sample) was mixed with 50 μL of internal standard solution [a 2,500 ng/mL solution of (S)-5-((1-benzylpyrrolidin-3-yl)(methyl) amino)-6-methyl-N-(thiazol-4-yl)pyridine-2-sulfonamide in deionized water/acetonitrile (1:1 v/v)], followed by addition of 50 μL of 6% (v/v) phosphoric acid in water. This was followed by the addition of 200 μL of acetonitrile. The samples were vortexed for 30 seconds and then centrifuged for 20 min at 13,000 rpm (15,871×g). The supernatants were further diluted four-fold with acetonitrile:water (1:1 v/v) and transferred to a 96-well plate prior to analysis. Calibration and QC samples were prepared in blank K2EDTA mouse plasma in the concentration range from 2.3 ng/mL to 4800 ng/mL with QC samples, including low QC (14 ng/mL), mid QC (225 ng/mL), and high QC (3600 ng/mL).

UHPLC-ESI-MS/MS analysis. Samples were then analyzed by ultra-high pressure liquid chromatography/electrospray ionization tandem mass spectroscopy (UHPLC-ESI MS/MS) using a Sciex™ TQ-5500 (AB Sciex™ LP, Concord, ON, Canada) mass spectrometer equipped with a Shimadzu Nexera™ UHPLC pump, column compartment and auto-sampler (Shimadzu Scientific Instruments, Inc., Columbia, MD, USA), using a binary gradient elution starting with 80% water (A)/20% acetonitrile (B), both solvents containing 0.1% formic acid. After 0.6 minutes, mobile phase B was increased linearly to 100% to 1 minute and elution was maintained at 100% mobile phase B until 1.5 minutes, and then allowed to re-equilibrate at the initial ration of 80% mobile phase A and 20% mobile phase B for a total run time of 2.5 minutes at a flow rate of 0.4 mL/min. The column used was ACE Excel™ 2 C18-PFP (2.1 mm i.d.×5.0 mm length, 2 μm particle size)(Advanced Chromatography Technologies Ltd, Aberdeen, Scotland). The analytes and the internal standard were ionized by electrospray in the positive ion mode and detected by multiple reaction monitoring (MRM) using the transitions listed in Table 1.

TABLE 1

Multiple Reaction Monitoring (MRM) for Fenfluramine, Norfenfluramine and the Internal Standard

| Compound | Precursor Ion (m/z) | Fragment Ion (m/z) | DP (V) | CE (eV) | CXP (V) | RT (min) |
|---|---|---|---|---|---|---|
| Fenfluramine | 232.0 | 158.9 | 300 | 30 | 10 | 1.49 |
| Norfenfluramine | 204.1 | 158.8 | 300 | 25 | 10 | 1.44 |
| Internal standard | 464.02 | 91.0 | 776 | 67 | 12 | 1.42 |

DP = Declustering potential,
CE = collision energy,
CXP = Exit potential,
RT = retention time Results. Animals were randomly assigned to vehicle (n=16) or different dose groups (n=16 per dose) and the 6 Hz assay was performed by an experimenter blinded to the treatment conditions. (rac)-Fenfluramine and (R)-fenfluramine, when administered to animals at 20 mg/kg, both showed a similar trend in the percentage of mice that were protected against psychomotor seizures (FIG. 1). The percentage of animals that were protected by (rac)-fenfluramine was 37.5% (p=0.018 by Fisher's exact test), and by (R)-fenfluramine was 31.3% (p=0.043), and by the vehicle only (control) was 0%. Similarly, administration of (rac)-norfenfluramine and (R)-norfenfluramine to animals at 20 mg/kg showed similar protection levels against psychomotor seizures (FIG. 1). The percentage of animals that were protected by (rac)-norfenfluramine was 50% (p=0.002 by Fisher's exact test), and by (R)-norfenfluramine was 50% (p=0.002), and by the vehicle only (control) was 0%.

UHPLC-ESI-MS/MS analysis of brain and plasma samples collected from mice immediately after efficacy testing in the 6 Hz assay revealed the following total brain and plasma concentrations of the administered compounds (Table 2):

TABLE 2

Analysis of Fenfluramine/Norfenfluramine Biodistribution In Vivo

| Compound (20 mg/kg) | Brain | Plasma |
|---|---|---|
| (rac)-Fenfluramine | 146.5 μM (33870 ng/g) | 10.74 μM (2484 ng/g) |
| (R)-Fenfluramine | 193.7 μM (44797 ng/g) | 15.02 μM (3474 ng/g) |
| (rac)-Norfenfluramine | 151.2 μM (30718 ng/g) | 12.97 μM (2636 ng/g) |
| (R)-Norfenfluramine | 179.6 μM (36501 ng/g) | 17.73 μM (3604 ng/g) |

In summary, in the 6 Hz assay both fenfluramine and norfenfluramine exhibited protective activity against seizures in the 6 Hz psychomotor seizure assay. (R)-Enantiomers of fenfluramine and norfenfluramine provided similar levels of seizure protection in the 6 Hz assay when compared with the racemic preparations of fenfluramine and norfenfluramine.

6.3.7. Biological Example 7. Anticonvulsant Effects of (R/S)-Fenfluramine and (R)-Fenfluramine in the Audiogenic Seizure Test DBA/2 is a widely used inbred strain of mouse susceptible to audiogenic seizures due to the asp2 mutation. Nearly 100% of the DBA/2 strain of mice undergo an age dependent susceptibility to audiogenic seizures and exhibit wild running followed by clonic convulsions and a tonic extension, often ending in respiratory arrest and death when exposed to a high intensity sound (DeSarro et al., 2017 *Epilepsy Behav.* 71:165-173). The objective of this study was to evaluate the anticonvulsant activity of (R/S)-fenfluramine and to compare it to (R)-fenfluramine in the DBA/2 mouse.

The method follows that described by Dilrmuiller et al., *Neuroreport* 4(6):683-686. Mice (DBA/2, 3-4 weeks old) were individually transferred (at 3-5 minute intervals) from the preparation room into an adjacent experimental room and placed in a Plexiglas™ jar (Diameter=40 cm; Height=35 cm) mounted with an electric bell (110-120 dB). Upon activating the bell, the occurrences and latencies to wild running fits, clonic and tonic seizures were measured. The number of deaths was also recorded. An audiogenic response score was assigned to each mouse as 0 (no seizure), 1 (wild running), 2 (clonic convulsion), 3 (tonic extension), or 4 (death). The bell was activated until a tonic seizure occurred or for a maximum of 60 seconds. Ten (10) mice were studied per group. The test was performed blind. All test compounds were dissolved in 0.9% saline (vehicle) and were administered by intraperitoneal (IP) injection at a dose volume of 10 mL/kg. Vehicle alone, (R/S)-fenfluramine (15 or 30 mg/kg) or (R)-fenfluramine (30 mg/kg) were administered 60 minutes prior to seizure induction. The positive reference compound (valproate; 180 mg/kg) was administered 30 minutes prior to seizure induction.

FIG. 2 and Table 3 show the results of the anticonvulsant effects of (R/S)-fenfluramine and (R)-fenfluramine in the mouse audiogenic seizure test utilizing male DBA/2 mice (n=10/group).

In vehicle controls, all DBA/2 mice showed wild running followed by clonic and tonic convulsions. The convulsive symptoms were observed with a mean latency comprised between 2.8±0.4 and 8.1±0.8 seconds after triggering the bell. Two mice died out of the 10 tested. The overall audiogenic response score was 3.2±0.13. (R/S)-Fenfluramine (15 and 30 mg/kg) dose-dependently decreased the number of mice showing clonic convulsions (−40% and −90%, respectively) and tonic convulsions (−100% for each dose), and increased the latencies to clonic (+441% and +853%, respectively) and tonic convulsions (+641% for each dose). The overall audiogenic response score was reduced by 50% and 72% at 15 and 30 mg/kg, respectively. (R)-Fenfluramine (30 mg/kg) decreased the number of mice showing clonic convulsions (−40%), fully suppressed tonic convulsions (−100%) and increased the latency to clonic and tonic convulsions (+450% and +641%, respectively). The overall audiogenic response score was reduced by 50%.

These results demonstrate a clear anticonvulsant activity for (R/S)-fenfluramine at 15 and 30 mg/kg and (R)-fenfluramine at 30 mg/kg in the audiogenic seizure test in the DBA/2 mouse. The magnitude of the anticonvulsant effect was comparable between (RI/S)-fenfluramine at 15 mg/kg and (R)-fenfluramine at 30 mg/kg.

TABLE 3

Summary of the anticonvulsant effects of (R/S)-Fenfluramine or (R)-Fenfluramine in the mouse audiogenic seizure test utilizing male DBA/2 mice (n = 10/group)

| Treatment | Dose (mg/kg) | Audiogenic Response Score | Wild Running Incidence (%) | Wild Running Latency (s) | Clonic Convulsion Incidence (%) | Clonic Convulsion Latency (s) | Tonic Extension Incidence (%) | Tonic Extension Latency (s) |
|---|---|---|---|---|---|---|---|---|
| Vehicle | 0 | 3.2 ± 0.13 | 100 | 2.8 ± 0.4 | 100 | 5.8 ± 0.7 | 100 | 8.1 ± 0.8 |
| (R/S)- | 15 | 1.6 ± 0.16 | 100 | 4.0 ± 0.7 | 60 | 31.4 ± 7.8 | 0 | 60.0 ± 0.0 |
| Fen | 30 | 0.9 ± 0.18 | 80 | 16.6 ± 7.4 | 10 | 55.3 ± 4.8 | 0 | 60.0 ± 0.0 |
| (R)-Fen | 30 | 1.6 ± 0.16 | 100 | 5.0 ± 1.4 | 60 | 31.9 ± 7.7 | 0 | 60.0 ± 0.0 |
| Valproate | 180 | 0.4 ± 0.16 | 40 | 38.1 ± 9.0 | 0 | 60.0 ± 0.0 | 0 | 60.0 ± 0.0 |

Audiogenic response score and latency data are presented as mean ± SEM.

All of the U.S. patents, U.S. patent application publications, U.S. patent applications, foreign patents, foreign patent applications and non-patent publications referred to in this specification are incorporated herein by reference in their entireties, including U.S. Provisional Application No. 62/711,051, filed Jul. 27, 2018.

Although the foregoing compounds, compositions, methods, and uses have been described in some detail to facilitate understanding, it will be apparent that certain changes and modifications may be practiced within the scope of the appended claims. Accordingly, the described embodiments are to be considered as illustrative and not restrictive, and the claimed invention is not to be limited to the details given herein, but may be modified within the scope and equivalents of the appended claims.

What is claimed is:

1. A method of treating epilepsy or an epileptic seizure disorder, comprising administering to a human subject in need thereof a therapeutically effective amount of (R)-norfenfluramine or a pharmaceutically acceptable salt thereof;

wherein the (R)-norfenfluramine or pharmaceutically acceptable salt thereof has an enantiomeric excess (ee) greater than 80%.

2. The method of claim 1, wherein the subject suffers from Dravet syndrome.

3. The method of claim 1, wherein the (R)-norfenfluramine or pharmaceutically acceptable salt thereof has an ee greater than 90%.

4. The method of claim 1, wherein the (R)-norfenfluramine or pharmaceutically acceptable salt thereof has an ee greater than 95%.

5. The method of claim 1, wherein the (R)-norfenfluramine or pharmaceutically acceptable salt thereof has an ee greater than 97%.

6. The method of claim 1, wherein the (R)-norfenfluramine or pharmaceutically acceptable salt thereof has an ee greater than 99%.

7. The method of claim 1, wherein the (R)-norfenfluramine or pharmaceutically acceptable salt thereof has an ee between 90% and 99%.

8. The method of claim 1, wherein administering the (R)-norfenfluramine or pharmaceutically acceptable salt thereof reduces the frequency of epileptic seizures in the subject.

9. The method of claim 1, wherein administering the (R)-norfenfluramine or pharmaceutically acceptable salt thereof reduces seizure frequency or mean convulsive frequency in the subject from baseline by at least 20%.

10. The method of claim 1, wherein the (R)-norfenfluramine or pharmaceutically acceptable salt thereof reduces seizure frequency or mean convulsive frequency in the subject from baseline by at least 35%.

11. The method of claim 1, wherein the (R)-norfenfluramine or pharmaceutically acceptable salt thereof reduces seizure frequency or mean convulsive frequency in the subject from baseline by at least 50%.

12. The method of claim 1, wherein administering the (R)-norfenfluramine or pharmaceutically acceptable salt thereof reduces seizure frequency or mean convulsive frequency in the subject from baseline by at least 60%.

13. The method of claim 1, wherein administering the (R)-norfenfluramine or pharmaceutically acceptable salt thereof reduces seizure frequency or mean convulsive frequency in the subject from baseline by at least 70%.

14. The method of claim 1, wherein administering the (R)-norfenfluramine or pharmaceutically acceptable salt thereof reduces seizure frequency or mean convulsive frequency in the subject from baseline by at least 80%.

15. The method of claim 1, wherein the (R)-norfenfluramine or pharmaceutically acceptable salt thereof is administered at a dose of about 0.1 mg/kg to about 50 mg/kg.

16. The method of claim 1, wherein the (R)-norfenfluramine or pharmaceutically acceptable salt thereof is administered at a dose of about 0.1 mg/kg to about 10 mg/kg.

17. The method of claim 1, wherein the (R)-norfenfluramine or pharmaceutically acceptable salt thereof is administered at a dose of about 0.5 mg/kg to about 2.5 mg/kg.

18. The method of claim 1, wherein the (R)-norfenfluramine or pharmaceutically acceptable salt thereof is administered at a dose of about 1 mg/kg to about 2 mg/kg.

19. A method of treating epilepsy or an epileptic seizure disorder, comprising administering to a human subject in need thereof a therapeutically effective amount of racemic norfenfluramine or a pharmaceutically acceptable salt thereof;

wherein the racemic norfenfluramine or pharmaceutically acceptable salt thereof is administered in combination with a therapeutically effective amount of phentermine or a pharmaceutically acceptable salt thereof.

20. The method of claim 19, wherein administering the racemic norfenfluramine or pharmaceutically acceptable salt thereof in combination with phentermine or a pharmaceutically acceptable salt thereof reduces seizure frequency or mean convulsive frequency in the subject from baseline by at least 20%.

21. The method of claim 1, wherein the (R)-norfenfluramine or pharmaceutically acceptable salt thereof is administered in combination with a therapeutically effective amount of phentermine or a pharmaceutically acceptable salt thereof.

22. The method of claim 1, wherein the (R)-norfenfluramine or pharmaceutically acceptable salt thereof has an ee between 80% and 99%.

23. The method of claim 1, wherein the (R)-norfenfluramine or pharmaceutically acceptable salt thereof has an ee between 80% and 99.5%.

* * * * *